United States Patent

Kamachi et al.

[11] Patent Number: 4,507,487
[45] Date of Patent: Mar. 26, 1985

[54] CHEMICAL COMPOUNDS

[75] Inventors: Hajime Kamachi, Urayasu; Jun Okumura, Yokohama; Takayuki Naito, Kawasaki; Masahisa Oka, Yokohama; Haruhiro Yamashita, Ichikawa, all of Japan

[73] Assignee: Bristol-Myers Company, New York, N.Y.

[21] Appl. No.: 536,024

[22] Filed: Sep. 26, 1983

Related U.S. Application Data

[62] Division of Ser. No. 422,632, Sep. 23, 1982.

[51] Int. Cl.$^3$ ............................................ C07D 277/42
[52] U.S. Cl. ........................................ 548/194; 544/27
[58] Field of Search ................................ 548/194, 195

[56] References Cited
U.S. PATENT DOCUMENTS
4,476,123 10/1984 Labeeuw ............................ 424/246

*Primary Examiner*—Robert Gerstl
*Attorney, Agent, or Firm*—Richard R. Lloyd

[57] ABSTRACT

Compounds of the formula

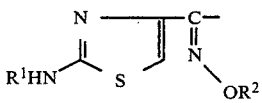

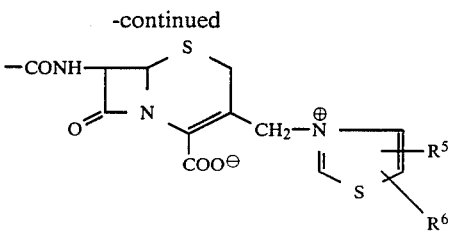

wherein $R^1$ is hydrogen or a conventional amino-protecting group, $R^2$ is a straight or branched chain alkyl group containing from 1 to 4 carbon atoms, allyl, 2-butenyl, 3-butenyl, propargyl, 2-butynyl, 3-butynyl, cycloalkyl containing from 3 to 6 carbon atoms or a group of the formula

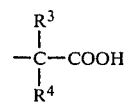

in which $R^3$ and $R^4$ each are independently hydrogen, methyl or ethyl, or $R^3$ and $R^4$, taken together with the carbon atom to which they are attached, may be a cycloalkylidene ring containing from 3 to 6 carbon atoms or a substituted cyclobutylidene ring of the formula

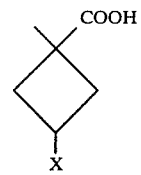

wherein X is halogen, hydroxy or (lower)alkoxy, and $R^5$ and $R^6$ each are independently hydrogen, halogen, amino, carbamoyl, acylamino, acyloxy, (lower)alkyl, (lower)alkenyl, (lower)alkoxy, (lower)alkylamino or (lower)alkylthio, in which each (lower)alkyl, (lower)alkoxy, (lower)alkylamino or (lower)alkylthio group may contain 1 or 2 substituents selected from amino, carboxy, halogen and nontoxic pharmaceutically acceptable acid addition salts, physiologically hydrolyzable esters and solvates thereof, as well as processes for their preparation, are disclosed. The compounds in which $R^1$ is hydrogen are potent antibacterial agents.

3 Claims, No Drawings

CHEMICAL COMPOUNDS

CROSS REFERENCE TO RELATED APPLICATIONS

This application is a divisional of our prior, co-pending application Ser. No. 422,632, filed Sept. 23, 1982.

This invention relates to novel cephalosporin derivatives of the formula

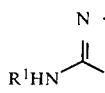
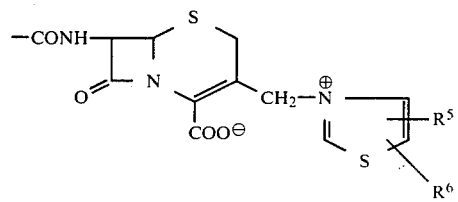

wherein $R^1$ is hydrogen or a conventional amino-protecting group, $R^2$ is a straight or branched chain alkyl group containing from 1 to 4 carbon atoms, allyl, 2-butenyl, 3-butenyl, propargyl, 2-butynyl, 3-butynyl, cycloalkyl containing from 3 to 6 carbon atoms or a group of the formula

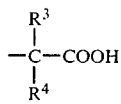

in which $R^3$ and $R^4$ each are independently hydrogen, methyl or ethyl, or $R^3$ and $R^4$, taken together with the carbon atom to which they are attached, may be a cycloalkylidene ring containing from 3 to 6 carbon atoms or a substituted cyclobutylidene ring of the formula

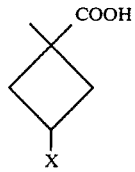

wherein X is halogen, hydroxy or (lower)alkoxy, and $R^5$ and $R^6$ each are independently hydrogen, halogen, amino, carbamoyl, acylamino, acyloxy, (lower)alkyl, (lower)alkenyl, (lower)alkoxy, (lower)alkylamino or (lower)alkylthio, in which each (lower)alkyl, (lower)alkoxy, (lower)alkylamino or (lower)alkylthio group may contain 1 or 2 substituents selected from amino, carboxy, halogen and hydroxy; and nontoxic pharmaceutically acceptable salts, physiologically hydrolyzable esters and solvates thereof. Processes for their preparation also are described.

DESCRIPTION OF THE PRIOR ART

U.K. Patent Specification No. 1,399,086 contains a generic disclosure encompassing a vast number of cephalosporins of the formula

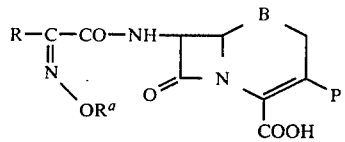

wherein R is hydrogen or an organic group, $R^a$ is an etherifying monovalent organic group linked to the oxygen through a carbon atom, B is $>S$ or $>S{\rightarrow}O$, and P is an organic group. However, the 2-aminothiazol-4-yl group is not identified as a possible R substituent. Although P may be the group —$CH_2Y$ in which Y may be the residue of a nitrogen-containing heterocycle, only pyridinium and 4-carbamoylpyridinium are exemplified, and there is no suggestion that Y may be the thiazolio moiety. U.S. Pat. No. 3,971,778 and its divisionals U.S. Pat. Nos. 4,024,133, 4,024,137, 4,064,346, 4,033,950, 4,079,178, 4,091,209, 4,092,477 and 4,093,803 have similar disclosures.

U.S. Pat. No. 4,278,793 contains a generic disclosure encompassing a vast number of cephalosporin derivatives of the formula

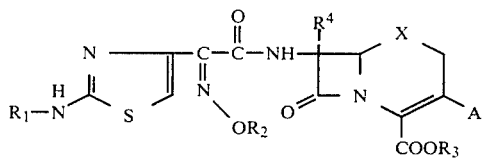

in which the variables $R_1$, $R_2$, $R_3$, $R_4$, X and A include generic definitions of the corresponding substituents of the compounds of Formula 1 claimed herein. Substituent A may be the group —$CH_2Y$ in which Y may be the residue of a nucleophilic group (the only heterocyclic rings disclosed for Y are pyridinium, quinolinium and isoquinolinium). In the 20 columns of definitions of the various substituent groups, the 78 page long table of structural formulae and the 225 examples, there is no disclosure that A may be the thiazolio moiety. United Kingdom Patent Specification No. 1,604,971 is concordant thereto and has a substantially identical disclosure. Published United Kingdom Patent Application No. 2,028,305 A, although apparently not formally related, contains the same broad generic disclosure but exemplifies A only as hydrogen.

U.S. Pat. No. 4,278,671 discloses 7-[2-(2-aminothiazol-4yl)-2-(syn)-methoxyiminoacetamido]cephalosporin derivatives of the formula

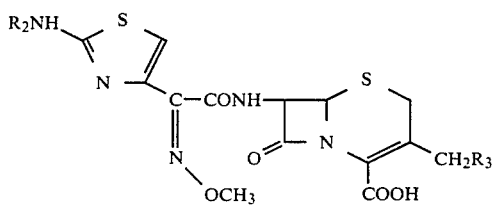

in which $R_2NH$ is an optionally protected amino group and $R_3$ is hydrogen or "the residue of a nucleophilic compound". The term "the residue of a nucleophilic compound" is broadly defined and it is then stated that $R^3$ "may alternatively be a quaternary ammonium group". Only pyridinium, variously substituted pyridinium, quinolinium, picolinium and lutidinium are disclosed as possible quaternary ammonium groups. There is no suggestion that the quaternary ammonium group may be the thiazolio moiety. United Kingdom Patent Specification No. 1,581,854 is concordant thereto and has a substantially identical disclosure. Other patents to the same patentee, which are not formally related but which have similar disclosures, include U.S. Pat. No. 4,098,888 and its divisionals U.S. Pat. Nos. 4,203,899, 4,205,180, 4,298,606 and United Kingdom Patent Specification No. 1,536,281.

COMPLETE DISCLOSURE

This invention relates to novel cephalosporin derivatives of the formula

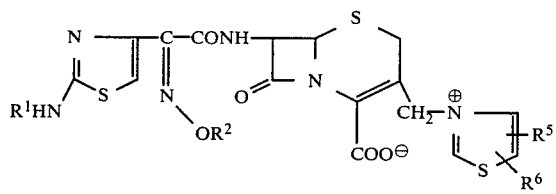

wherein $R^1$ is hydrogen or a conventional amino-protecting group, $R^2$ is a straight or branched chain alkyl group containing from 1 to 4 carbon atoms, allyl, 2-butenyl, 3-butenyl, propargyl, 2-butynyl, 3-butynyl, cycloalkyl containing from 3 to 6 carbon atoms or a group of the formula

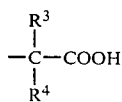

in which $R^3$ and $R^4$ each are independently hydrogen, methyl or ethyl, or $R^3$ and $R^4$, taken together with the carbon atom to which they are attached, may be a cycloalkylidene ring containing from 3 to 6 carbon atoms or a substituted cyclobutylidene ring of the formula

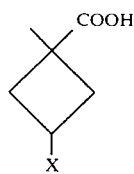

wherein X is halogen, hydroxy or (lower)alkoxy, and $R^5$ and $R^6$ each are independently hydrogen, halogen, amino, carbamoyl, acylamino, acyloxy, (lower)alkyl, (lower)alkenyl, (lower)alkoxy, (lower)alkylamino or (lower)alkylthio, in which each (lower)alkyl, (lower)alkoxy, (lower)alkylamino or (lower)alkylthio group may contain 1 or 2 substituents selected from amino, carboxy, halogen and hydroxy, and nontoxic pharmaceutically acceptable salts, physiologically hydrolyzable esters and solvates thereof, as well as processes for their preparation. Also included within the scope of this invention are the solvates (including hydrates) of the compounds of Formula I, as well as the tautomeric forms of the compounds of Formula I, e.g. the 2-iminothiazolin-4-yl form of the 2-aminothiazol-4-yl moiety.

As shown in the structural formula, the compounds of Formula I have the "syn" or "Z" configuration with respect to the alkoxyimino group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers.

The nontoxic pharmaceutically acceptable acid addition salts of the compounds of Formula I include, for example, the salts with hydrochloric, hydrobromic, formic, nitric, sulfuric, methanesulfonic, phosphoric, acetic and trifluoroacetic acids, and other acids which have been used in the penicillin and cephalosporin art.

The compounds of Formula I in which $R^1$ is hydrogen exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The preferred compounds of Formula I are those in which $R^1$ is hydrogen, $R^2$ is methyl, ethyl, propargyl or a group of the formula

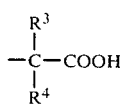

in which $R^3$ and $R^4$ each are methyl, or $R^3$ and $R^4$, taken together with the carbon atom to which they are attached, are cyclopropylidene or cyclobutylidene, $R^5$ is hydrogen, (lower)alkyl or (lower)alkylthio, and $R^6$ is hydrogen, amino, (lower)alkylthio, (lower)alkyl, (lower)alkoxy, amino(lower)alkyl, acylamino or hydroxy(lower)alkyl. Particularly preferred compounds are those in which $R^1$ is hydrogen, $R^2$ is methyl, ethyl, propargyl, 2-carboxyprop-2-oxyimino or 1-carboxycyclobut-1-oxyimino, $R^5$ is hydrogen or (lower)alkyl, and $R^6$ is hydrogen, amino, (lower)alkyl or (lower)alkylthio. The most preferred compounds of the invention are (1) 7-[(Z)-2-(2-aminothiazol-4-yl)-2-(2-carboxyprop-2-oxyimino)acetamido]-3-(2-methylthiothiazolio)methyl-3-cephem-4-carboxylate, (2) 7-[(Z)-2-(2-aminothiazol-4-yl)-2-(1-carboxycyclobut-1-oxyimino)acetamido]-3-(2-methylthiothiazolio)methyl-3-cephem-4-carboxylate, (3) 7-[(Z)-2-(2-aminothiazol-4-yl)-2-(methoxyimino)acetamido]-3-(2-methylthiothiazolio)methyl-3-cephem-4-carboxylate, (4) 7-[(Z)-2-(2-aminothiazol-4-yl)-2-(ethoxyimino)acetamido]-3-(2-methylthiothiazolio)methyl-3-cephem-4-carboxylate, (5) 7-[(Z)-2-(2-aminothiazol-4-yl)-2-(2-carboxyprop-2-oxyimino)acetamido]-3-thiazoliomethyl-3-cephem-4-carboxylate, (6) 7-[(Z)-2-(2-Aminothiazol-4-yl)-2-(2-carboxyprop-2-oxyimino)acetamido]-3-[5-(2-hydroxyethyl)-4-methylthiazolio]methyl-3-cephem-4-carboxylate, (7) 7-[(Z)-2-(2-aminothiazol-4-yl)-2-(2-carboxyprop-2-oxyimino)acetamido]-3-(4-methylthiazolio)methyl-3-cephem-4-carboxylate, (8) 7-[2-(Z)-(2-aminothiazol-4-yl)-2-(1-carboxycyclobut-1-oxyimino)acetamido]-3-(2-methylthiazolio)-methyl-3-cephem-4-carboxylate, (9) 7-[(Z)-2-(2-aminothiazol-4-yl)-2-(2-carboxyprop-2-oxyimino)acetamido]-3-(4-methyl-2-methylthiothiazolio)methyl-3-cephem-4-carboxylate and

(10) 7-[(Z)-2-(2-aminothiazol-4-yl)-2-propargyloxyiminoacetamido]-3-(2-methylthiothiazolio)methyl-3-cephem-4-carboxylate.

In the primary evaluation of the compounds of this invention, the Minimum Inhibitory Concentrations (MIC's) of the compounds were determined by the two-fold serial agar dilution method in Mueller-Hinton agar against 32 strains of test organisms in six groups. The geometric means of the MIC's determined in these tests are shown in Table 1.

The MIC's of some of the preferred compounds against specific test organisms are shown in Table 2. The test method was as described for Table 1.

TABLE 1

| Compound of Example | Geometric Mean of MIC (mcg/mL) | | | | | |
|---|---|---|---|---|---|---|
| | (G+)-Ia (5 strains) | (G+)-Ib (5) | (G−)-Ia (5) | (G−)-Ib (6) | (G−)-II (5) | (G−)-III (6) |
| 1 = (Ia) | 1.2 | 3.6 | 0.038 | 0.69 | 0.24 | 1.4 |
| 2 = (Ib) | 0.92 | 2.7 | 0.025 | 0.4 | 0.2 | 1.8 |
| 3 = (Ic) | 0.23 | 0.8 | 0.022 | 0.15 | 0.14 | 2.0 |
| 4 = (Id) | 0.35 | 0.61 | 0.076 | 0.32 | 0.69 | 5.6 |
| 5 = (Ie) | 8.3 | 25 | 0.13 | 2.5 | 3.6 | 3.1 |
| 6 = (If) | 8.3 | 25 | 0.076 | 1.8 | 2.8 | 4.4 |
| 7 = (Ig) | 7.2 | 12.5 | 0.076 | 1.8 | 2.8 | 4.0 |
| 8 = (Ih) | 5.5 | 14 | 0.15 | 4.0 | 8.3 | 5.6 |
| 9 = (Ii) | 9.5 | 16 | 0.10 | 1.6 | 2.8 | 6.3 |
| 10 = (Ij) | 2.1 | 6.3 | 0.8 | 1.4 | 5.5 | 22 |
| 11 = (Ik) | 4.2 | 9.5 | 0.076 | 1.6 | 0.4 | 2.1 |
| 12 = (Im) | 1.8 | 4.7 | 0.066 | 0.79 | 0.4 | 5.7 |
| 13 = (In) | 25 | 50 | 0.26 | 4.0 | 1.6 | 23 |
| 14 = (Io) | 5.5 | 12.5 | 0.15 | 3.6 | 3.2 | 7.0 |
| 15 = (Ip) | 7.2 | 25 | 0.4 | 5.5 | 3.6 | 13 |
| 16 = (Iq) | 4.2 | 19 | 0.1 | 0.79 | 0.53 | 2.8 |
| 17 = (Ir) | 0.23 | 0.8 | 0.66 | 0.6 | 0.69 | 6.9 |

(G+)-Ia: Penicillin-sensitive *S. aureus* (5 strains)
(G+)-Ib: Penicillin-resistant *S. aureus* (5 strains)
(G−)-Ia: Cephalothin-sensitive *E. coli* (2 strains), *Kl. pneumoniae* (1 strain) and *Pr. mirabilis* (2 strains)
(G−)-Ib: Cephalothin-resistant *E. coli* (3 strains) and *Kl. pneumoniae* (3 strains)
(G−)-II: *M. morganii* (1 strain), *Ent. cloacae* (2 strains) and *Ser. marcescens* (2 strains)
(G−)-III: *Ps. aeruginosa* (6 strains)

TABLE 2

Minimum Inhibitory Concentrations (mcg/ml) Against Various Microorganisms

| Organism | Compound | | | |
|---|---|---|---|---|
| | Example 1 (Ia) | Example 2 (Ib) | Example 3 (Ic) | Example 4 (Id) |
| *S. aureus* Smith | 1.6 | 1.6 | 0.4 | 0.4 |
| *S. aureus* BX-1633-2* | 3.1 | 3.1 | 0.8 | 0.4 |
| *E. coli* Juhl | 0.1 | 0.1 | 0.025 | 0.1 |
| *E. coli* A15164** | 0.8 | 0.4 | 0.1 | 0.2 |
| *K. pneumoniae* D11 | 0.1 | 0.05 | 0.025 | 0.1 |
| *K. pneumoniae* A9867** | 1.6 | 3.1 | 0.8 | 1.6 |
| *Pr. mirabilis* A9554 | 0.05 | 0.025 | 0.05 | 0.2 |
| *M. morganii* A9553 | 0.1 | 0.2 | 0.2 | 0.4 |
| *Ent. cloacae* A9656 | 0.1 | 0.05 | 0.05 | 0.2 |
| *Ser. marcescens* A20019 | 0.1 | 0.1 | 0.025 | 0.1 |
| *Ps. aeruginosa* A15150 | 0.8 | 0.8 | 0.8 | 3.1 |
| *Ps. aeruginosa* A9843 | 1.6 | 1.6 | 3.1 | 12.5 |
| *Ps. aeruginosa* A20717 | 3.1 | 6.3 | 6.3 | 12.5 |

*Pencillin-resistant strain
**Cephalothin-resistant strain

The absorption of some of the preferred compounds were determined in mice following a single intramuscular injection of the test compound (dissolved in 0.1M phosphate buffer; pH 7) at a dosage of 10, 20 or 40 mg/kg. Blood samples were collected from the orbital sinuses into heparinized capillary tubes and assayed in Nutrient Agar (pH 6.6) using *E. coli* Ess-22-31 as the test organism. The blood levels at various time intervals, the half-life values ($t_{\frac{1}{2}}$) and the areas under the curve (AUC) are shown in Table 3.

TABLE 3

| Compound of Example | Dose mg/kg (im) | Mouse Blood Levels | | | | | | | | T ½ (min) | AUC (mcg · hr/ml) |
|---|---|---|---|---|---|---|---|---|---|---|---|
| | | Mouse Blood Level (mcg/ml) Minutes After Administration | | | | | | | | | |
| | | 10 | 20 | 30 | 40 | 50 | 60 | 90 | 120 | | |
| 1 = (Ia) | 40 | 51 | 40 | 29 | 15 | 9.0 | 4.6 | <3 | — | 13 | 25 |

| Compound of Example | Dose mg/kg (im) | Mouse Blood Level (mcg/ml) Minutes After Administration | | | | | | | | T½ (min) | AUC (mcg·hr/ml) |
|---|---|---|---|---|---|---|---|---|---|---|---|
| | | 10 | 20 | 30 | 40 | 50 | 60 | 90 | 120 | | |
| | 20 | 33 | 24 | 18 | 9.4 | 6.7 | 3.5 | <3 | — | 14 | 16 |
| | 10 | 12 | 7.4 | 4.7 | <3 | — | — | — | — | 15 | 5.0 |
| 2 = (Ib) | 40 | 43 | 27 | 14 | 7.5 | 3.8 | 2.3 | <1.6 | — | 11 | 16 |
| | 20 | 22 | 15 | 8.6 | 5.7 | 2.4 | <1.6 | — | — | 11 | 9.0 |
| | 10 | 8.4 | 5.5 | 3.7 | <1.6 | — | — | — | — | 17 | 3.6 |
| 3 = (Ic) | 40 | 48 | 36 | 32 | 32 | 24 | 20 | 15 | 10 | 54 | 60 |
| | 20 | 24 | 22 | 20 | 17 | 13 | 11 | 9.5 | 4.5 | 46 | 29 |
| | 10 | 14 | 14 | 12 | 10 | 9.8 | 6.8 | 5.2 | 3.2 | 47 | 18 |

In another aspect, this invention relates to processes for the preparation of the compounds of Formula I. There are two basic procedures for converting a readily available starting cephalosporin to another cephalosporin having different substituents on the 7- and 3-positions. One may first remove the 7-substituent and replace it with the desired 7-substituent, and then insert the desired 3-substituent. Alternatively, one may first insert the desired 3-substituent and subsequently exchange the 7-substituent. The compounds of Formula I may be prepared by either procedure and both are included within the scope of this invention, but it is preferred to insert the desired 7-substituent first and then insert the desired 3-substituent. The preferred procedure is shown below in Reaction Scheme 1 while alternative procedures are shown in Reaction Schemes 2 and 3. In each reaction scheme, n may be 0 or 1. The abbreviation "Tr" represents the trityl(triphenylmethyl) group, which is a preferred amino-protecting group. The abbreviation "Ph" represents the phenyl group. Thus, the —CH(Ph)$_2$ moiety is the benzhydryl group, which is a preferred carboxyl-protecting group. When R$^2$ is the

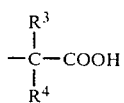

moiety it is desirable to protect the carboxyl group with a conventional carboxyl-protecting group such as the t-butyl moiety. Throughout the specification the "prime" symbol (') is used with specific compounds to indicate that the carboxyl group is protected, e.g. as in Compound III-4'.

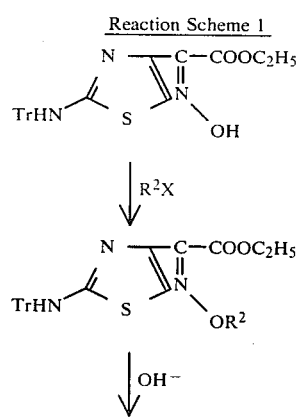

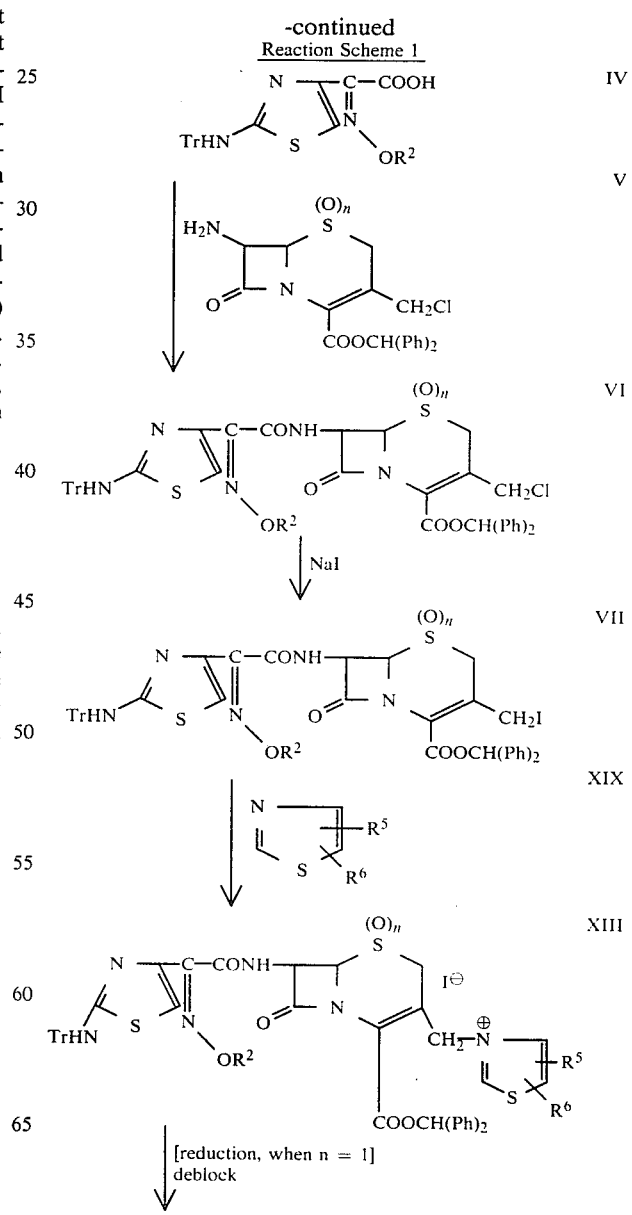

-continued
Reaction Scheme 1

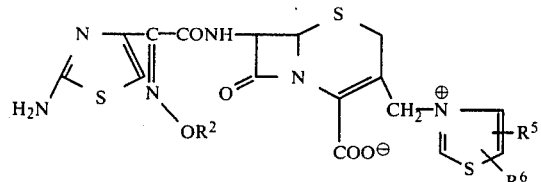

Reaction Scheme 2

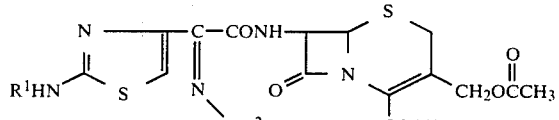

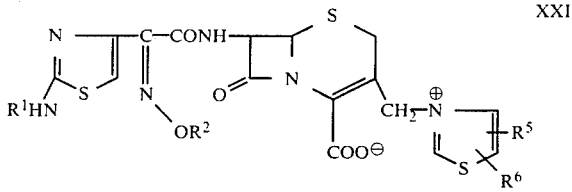

[reduction, when n = 1]
deblock

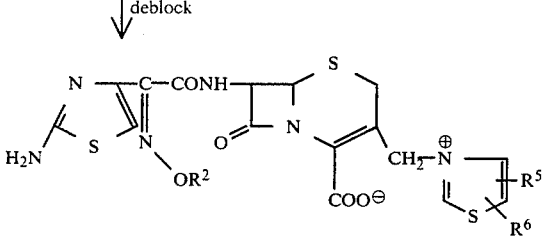

Reaction Scheme 3

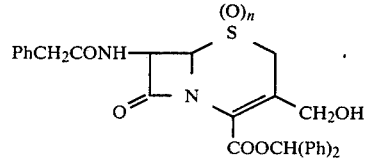

PCl₅
pyridine

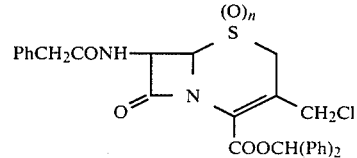

NaI

-continued
Reaction Scheme 3

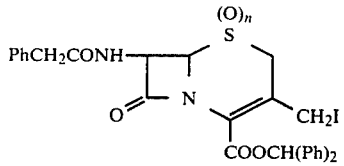

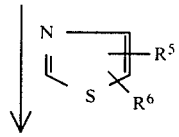

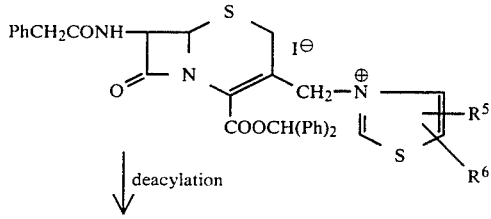

deacylation

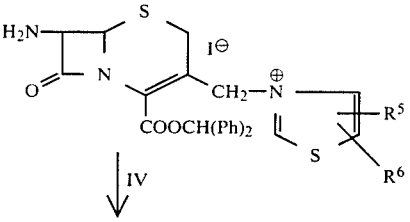

IV

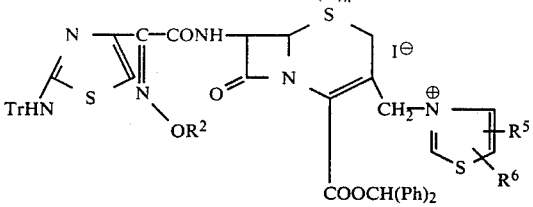

[reduction, when n = 1]
deblock

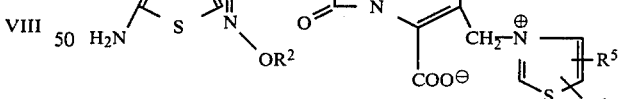

Although the above Reaction Schemes show preferred multi-step procedures for the preparation of the compounds of Formula I, it will be appreciated that other starting materials and procedures may be utilized to prepare the intermediates used in the key step of each Reaction Scheme. Thus, the key step in Reaction Scheme 1 is the reaction of Compound VII with the thiazole compound of Formula XIX. Compound VII may itself be prepared by other procedures. Similarly, the key step in Reaction Scheme 3 is the acylation of Compound XII with Compound IV. Both compounds XII and IV may be prepared by other procedures.

In Reaction Scheme 2, when reacting the thiazole compound of Formula XIX with the cephalosporin XX in its 3-acetoxymethyl form, it is preferred that potassium thiocyanate or potassium iodide be added to the reaction mixture to facilitate the quaternization reaction.

The present invention provides a process for the preparation of compounds of the formula

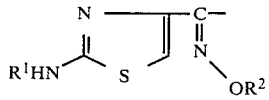   I

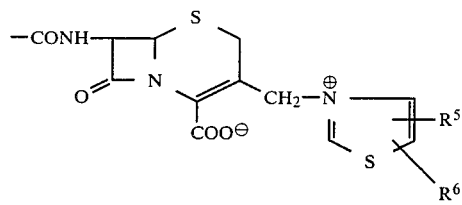

wherein R¹ is hydrogen or a conventional amino-protecting group, R² is a straight or branched chain alkyl group containing from 1 to 4 carbon atoms, allyl, 2-butenyl, 3-butenyl, propargyl, 2-butynyl, 3-butynyl, cycloalkyl containing from 3 to 6 carbon atoms or a group of the formula

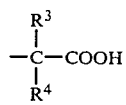

in which R³ and R⁴ each are independently hydrogen, methyl or ethyl, or R³ and R⁴, taken together with the carbon atom to which they are attached, may be a cycloalkylidene ring containing from 3 to 6 carbon atoms or a substituted cyclobutylidene ring of the formula

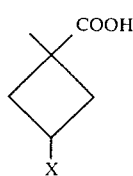

wherein X is halogen, hydroxy or (lower)alkoxy, and R⁵ and R⁶ each are independently hydrogen, halogen, amino, carbamoyl, acylamino, acyloxy, (lower)alkyl, (lower)alkenyl, (lower)alkoxy, (lower)alkylamino or (lower)alkylthio, in which each (lower)alkyl, (lower)alkoxy, (lower)alkylamino or (lower)alkylthio group may contain 1 or 2 substituents selected from amino, carboxy, halogen and hydroxy; and nontoxic pharmaceutically acceptable salts, physiologically hydrolyzable esters and solvates thereof, which process comprises reacting a compound of the formula

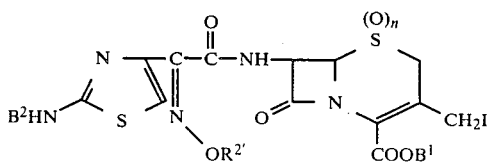   XIV in which R²′ is the same as R² or is a group of the formula

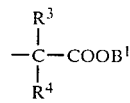

in which R³ and R⁴ are as defined above, B¹ is a conventional carboxyl-protecting group, B² is a conventional amino-protecting group and n is 0 or 1, with a thiazole compound of the formula

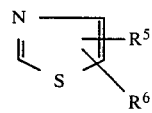   XIX in which R⁵ and R⁶ are as defined above, to produce a compound of the formula

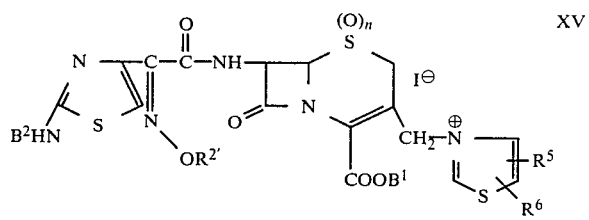   XV and, if n is 1, reducing the sulfoxide by conventional means, and subsequently removing all protecting groups by conventional means.

The present invention also provides a process for the preparation of compounds of the formula

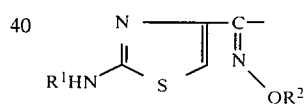   I

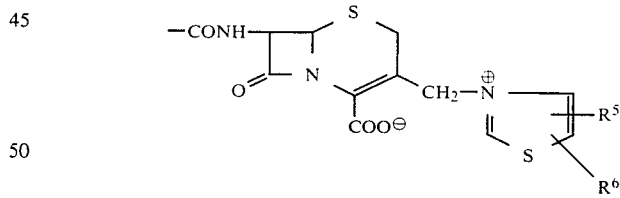

wherein R¹ is hydrogen or a conventional amino-protecting group, R² is a straight or branched chain alkyl group containing from 1 to 4 carbon atoms, allyl, 2-butenyl, 3-butenyl, propargyl, 2-butynyl, 3-butynyl, cycloalkyl containing from 3 to 6 carbon atoms or a group of the formula

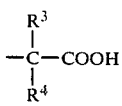

in which R³ and R⁴ each are independently hydrogen, methyl or ethyl, or R³ and R⁴, taken together with the carbon atom to which they are attached, may be a cycloalkylidene ring containing from 3 to 6 carbon atoms or a substituted cyclobutylidene ring of the formula

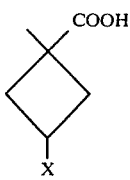

wherein X is halogen, hydroxy or (lower)alkoxy, and $R^5$ and $R^6$ each are independently hydrogen, halogen, amino, carbamoyl, acylamino, acyloxy, (lower)alkyl, (lower)alkenyl, (lower)alkoxy, (lower)alkylamino or (lower)alkylthio, in which each (lower)alkyl, (lower)alkoxy, (lower)alkylamino or (lower) alkylthio group may contain 1 or 2 substituents selected from amino, carboxy, halogen and hydroxy; and nontoxic pharmaceutically acceptable salts, physiologically hydrolyzable esters and solvates thereof, which process comprises reacting a compound of the formula

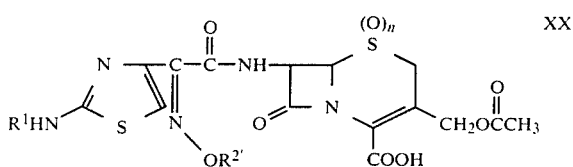

in which $R^1$ is as defined above, $R^{2'}$ is the same as $R^2$ or is a group of the formula

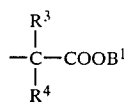

in which $R^3$ and $R^4$ are as defined above, $B^1$ is a conventional carboxyl-protecting group and n is 0 or 1, with a thiazole compound of the formula

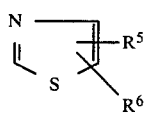

in which $R^5$ and $R^6$ are as defined above, to produce a compound of the formula

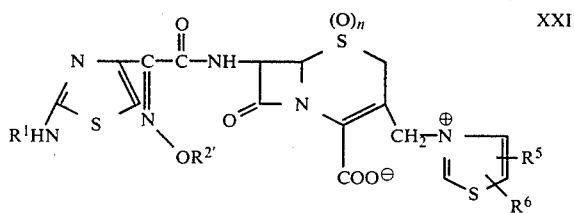

and, if n is 1, reducing the sulfoxide by conventional means, and subsequently removing any protecting group by conventional means.

The reactions are carried out in a non-aqueous organic solvent such as dimethyl sulfoxide, hexamethylphosphoramide, methylene chloride, chloroform, ethyl ether, hexane, ethyl acetate, tetrahydrofuran, acetonitrile and the like, or mixtures of such solvents. The reactions are conveniently carried out at a temperature of from about $-10°$ C. to about $+50°$ C.; we normally prefer to conduct the reactions at room temperature. At least one mole of the tertiary amine should be used per mole of Compound XIV or XX; we normally prefer to utilize from about 50% to 100% excess of the thiazole compound of Formula XIX.

Carboxyl-protecting groups suitable for use as $B^1$ in the above reactions are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl, and other carboxyl-protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl, formyl and trichloroethoxycarbonyl. Amino-protecting groups which are readily removed by treatment with acid, e.g. the trityl group, are preferred.

The present invention also provides a process for the preparation of compounds of the formula

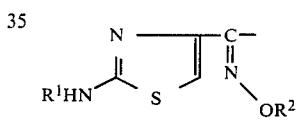

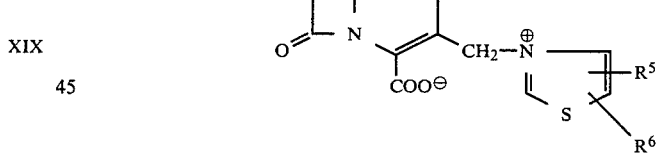

wherein $R^1$ is hydrogen or a conventional amino-protecting group, $R^2$ is a straight or branched chain alkyl group containing from 1 to 4 carbon atoms, allyl, 2-butenyl, 3-butenyl, propargyl, 2-butynyl, 3-butynyl, cycloalkyl containing from 3 to 6 carbon atoms or a group of the formula

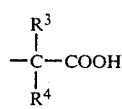

in which $R^3$ and $R^4$ each are independently hydrogen, methyl or ethyl, or $R^3$ and $R^4$, taken together with the carbon atom to which they are attached, may be a cycloalkylidene ring containing from 3 to 6 carbon atoms or a substituted cyclobutylidene ring of the formula

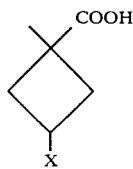

wherein X is halogen, hydroxy or (lower)alkoxy, and $R^5$ and $R^6$ each are independently hydrogen, halogen, amino, carbamoyl, acylamino, acyloxy, (lower)alkyl, (lower)alkenyl, (lower)alkoxy, (lower)alkylamino or (lower)alkylthio, in which each (lower)alkyl, (lower)alkoxy, (lower)alkylamino or (lower)alkylthio group may contain 1 or 2 substituents selected from amino, carboxy, halogen and hydroxy; and nontoxic pharmaceutically acceptable salts, physiologically hydrolyzable esters and solvates thereof, which process comprises reacting a compound of the formula

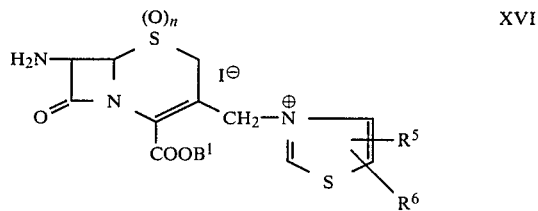

or an N-silyl derivative thereof, in which $B^1$ is hydrogen or a conventional carboxyl-protecting group, n is 0 or 1 and $R^5$ and $R^6$ are as defined above, with an acylating derivative of an acid of the formula

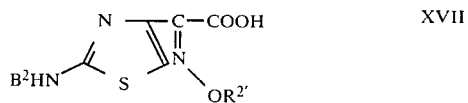

wherein $B^2$ is a conventional amino-protecting group and $R^{2'}$ is the same as $R^2$ or is a group of the formula

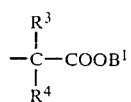

in which $R^3$ and $R^4$ are as defined above, to produce a compound of the formula

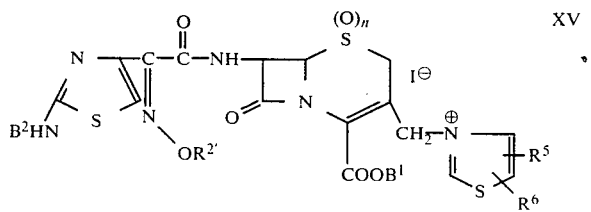

and, if n is 1, reducing the sulfoxide by conventional means, and subsequently removing all protecting groups.

The acylating derivatives of the acid of Formula XVII include the acid halides (and particularly the acid chloride), mixed acid anhydrides (such as the acid anhydrides formed with pivalic acid or a haloformate such as ethyl chloroformate), and activated esters (such as may be formed with N-hydroxybenztriazole in the presence of a condensing agent such as dicyclohexylcarbodiimide). The acylation may also be effected by use of the free acid of Formula XVII in the presence of a condensing agent such as dicyclohexylcarbodiimide, carbonyldiimidazole or an isoxazolium salt. As used herein, the term "acylating derivative" of the acid of Formula XVII includes the free acid itself in the presence of a condensing agent such as described above. The preferred acylating derivative of the acid of Formula XVII is the acid chloride, preferably used in the presence of an acid binding agent (and particularly a tertiary amine acid binding agent such as triethylamine, dimethylaniline or pyridine).

When the acylation is conducted with an acid halide it is possible to utilize an aqueous reaction medium, but a non-aqueous medium is preferred. When acid anhydrides, activated esters, or the free acid in the presence of a condensing agent, are used for the acylation, the reaction medium should be non-aqueous. Particularly preferred solvents for the acylation reaction are halogenated hydrocarbons such as methylene chloride and chloroform, but tertiary amides such as dimethylacetamide or dimethylformamide may be utilized, as well as other conventional solvents such as tetrahydrofuran, acetonitrile and the like.

The acylation reaction may be conducted at a temperature of from about −50° C. to about +50° C. However, it is preferably conducted at or below room temperature and most preferably from about −30° C. to about 0° C. It is usually preferred to acylate the compound of Formula XVI with about a stoichiometric amount of the acylating agent of Formula XVII, although a small excess (e.g. 5–25%) of the acylating agent may be utilized.

It is preferable that the compound of Formula XVI be acylated in the form of its N-silyl derivative (when utilizing a non-aqueous reaction medium). This is conveniently done in situ by simply adding a suitable silylating agent (e.g. N,O-bistrimethylsilylacetamide) to the solution of Compound XVI prior to the addition of the acylating agent of Formula XVII. We prefer to utilize about 3 moles of silylating agent per mole of Compound XVI although this is not critical. The silyl compound is readily removed after acylation by the addition of water.

When substituent $R^2$ of the acylating acid of Formula XVII is a group of the formula

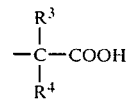

it is preferred that the acylating acid contain a carboxyl-protecting group, i.e. that the acylating acid be utilized in the form

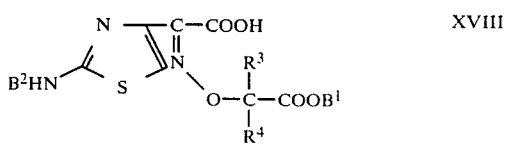

in which $B^2$ is a conventional amino-protecting group as described above, and $B^1$ is a conventional carboxyl-protecting group as described above.

We have found that the quaternization steps of Reaction Schemes 1 and 3 [the reaction of XIX with VII in Scheme 1 and the reaction of XIX with X in Scheme 3] generally requires a lengthy reaction time and/or a relatively high temperature to attain complete quaternization. In order to accelerate this reaction and thereby obtain good yields in a shorter period of time and/or a lower reaction temperature, we prefer to add silver tetrafluoroborate ($AgBF_4$) to the reaction mixture. The amount of $AgBF_4$ is not critical, but we generally prefer to utilize an amount which is about equimolar to the cephalosporin reactant of Formula VII or X.

The acylating acids of Formula XVII (and the corresponding precursor esters), including the carboxyl- and amino-protected derivatives [XVIII] thereof, are known in the art or may be prepared by known procedures. Thus, Compounds III-1, III-2 and III-3 (shown in Preparation No. 1, below) and Compounds IV-1, IV-2 and IV-3 (shown in Preparation No. 2, below) are described in Tetrahedron, 34, 2233–2243 (1978), in which they were prepared by a different route. Compounds IV-4' and IV-5', used as starting materials in Preparation No. 11 and Preparation No. 13, respectively, were prepared according to the general procedure described in U.S. Pat. No. 4,258,041 and published United Kingdom Patent Application No. 2,025,398. Compound III-7 was prepared by the procedure described in U.S. Pat. No. 4,294,960 and was hydrolyzed to Compound IV-7. Compounds III-6' and IV-6', both of which are new compounds, were prepared by a procedure similar to that utilized for the preparation of Compounds III-5' and IV-5', respectively (see Preparations Nos. 1 and 2).

The thiazole compounds of the formula

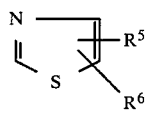

XIX wherein $R^5$ and $R^6$ are as described above are known compounds, or may be prepared by methods known in the art.

When utilizing Reaction Scheme 1, 2 or 3 in which the cephalosporin nucleus is in the form of the 1-oxide (n=1), the 1-oxide is prepared by known procedures such as oxidation with m-chloroperbenzoic acid, peracetic acid, etc. The 1-oxide subsequently may be reduced by known procedures, e.g. reduction of the corresponding alkoxysulfonium salt with iodide ion in an aqueous medium. The alkoxysulfonium salt itself is readily prepared by treatment of the 1-oxide with, for example, acetyl chloride.

Cephalosporins of Formula XX, which are used as starting materials in Reaction Scheme 2, are known in the art. See, for example, U.S. Pat. No. 4,258,041.

As used herein, the terms acylamino and acyloxy refer to an acylated amino or acylated hydroxy group in which the acyl moiety is (lower)alkanoyl (e.g. formyl, acetyl, propionyl, butyryl, isobutyryl, isovaleryl, etc.), aroyl (e.g. benzoyl, etc.), (lower)alkanesulfonyl (e.g. mesyl, ethanesulfonyl, etc.) or arylsulfonyl (e.g. benzenesulfonyl, tosyl, etc.).

As used herein, the terms "(lower)alkyl", "(lower)alkoxy", "(lower)alkylthio" (or the like) mean straight or branched chain alkyl, alkoxy, alkylthio (or the like) groups containing from 1 to 6 carbon atoms, inclusive.

In another embodiment, this invention relates to novel intermediates of the formula

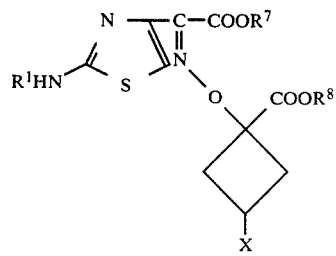

wherein $R^1$ is hydrogen or a conventional amino-protecting group, $R^7$ is hydrogen or (lower)alkyl, $R^8$ is hydrogen or a conventional carboxyl-protecting group and X is halogen, or, if $R^7$ or $R^8$ is hydrogen, a salt thereof. A preferred embodiment is (Z)-2-(1-t-butoxycarbonyl-3-chlorocyclobut-1-oxyimino)-2-(2-tritylaminothiazol-4-yl)acetic acid, or a salt or (lower)alkyl ester thereof. A particularly preferred alkyl ester is ethyl (Z)-2-(1-t-butoxycarbonyl-3-chlorocyclobut-1-oxyimino)-2-(2-tritylaminothiazol-4-yl)acetate.

PREPARATION No. 1

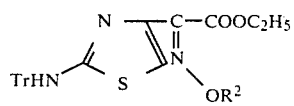

III

Ethyl (Z)-2-Methoxyimino-2-(2-tritylaminothiazol-4-yl)acetate (III-1)

A mixture of ethyl (Z)-2-hydroxyimino-2-(2-tritylaminothiazol-4-yl)acetate (II) (5.00 g, 10.9 mmoles), $CH_3I$ (2.04 mL, 32.8 mmoles) and $K_2CO_3$ (4.54 g, 32.8 mmoles) in dry dimethylsulfoxide (DMSO) (100 mL) was stirred at room temperature overnight and then poured into water (250 mL). The precipitate which formed was collected by filtration, washed with water and dried to give the title compound (5.15 g, quantitative yield). Mp. 115° C. (dec.).

NMR: $\delta^{CDCl_3}$ ppm 1.32 (3H, t), 3.98 (3H, s), 4.30 (2H, q), 6.42 (1H, s), 7.2 (1H, m), 7.25 (15H, s).

Compounds III-2, III-3, III-4', III-5', III-6' and III-7 were prepared by the general procedure set forth above, but replacing the methyl iodide with the appropriate iodide or bromide.

| Compound | $R^2$ (or $R^{2'}$) | Yield (%) | MP (°C.) | Literature Mp (°C.) |
|---|---|---|---|---|
| III-1 | methyl | 100 | 115 (dec.) | 120 (dec.)[1] |
| III-2 | ethyl | 67 | 97–98 | * |
| III-3 | allyl | * | * | * |
| III-4' | —C(CH₃)₂COOtButyl | 100 | 125–126 | 123.5–125[2]; 134[3] |
| III-5' | 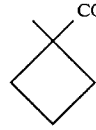COOtButyl | 68 | 81–83 | not reported[3] |

-continued

| Compound | R² (or R²') | Yield (%) | MP (°C.) | Literature Mp (°C.) |
|---|---|---|---|---|
| III-6' | 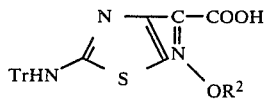 COOtButyl, Cl | 36 | 75–85 | (new compound) |
| III-7 | —CH₂C≡CH | 94 | 70–73 | not reported[4] |

*The ester was hydrolyzed without isolation
[1]Tetrahedron 34, 2233 (1978)
[2]U.S. Pat. No. 4,258,041
[3]U.S. Pat. No. 4,288,434
[4]U.S. Pat. No. 4,294,960

PREPARATION NO. 2

$$\text{TrHN} \underset{S}{\overset{N}{\diagdown}} \overset{C-COOH}{\underset{N}{\parallel}} \diagdown OR^2 \qquad IV$$

(Z)-2-Methoxyimino-2-(2-tritylaminothiazol-4-yl)acetic acid (IV-1)

The ethyl ester III-1 prepared in Preparation No. 1 (6.00 g, 12.7 mmoles) in ethanol (120 mL) was treated with 2N NaOH (12.7 mL) at room temperature overnight. The reaction mixture was adjusted to pH 8 by the addition of powdered dry ice and the solvent was evaporated under reduced pressure. The residue was dissolved in water (100 mL) and the solution was acidified with 1N HCl to pH 2 and then extracted with ethyl acetate (3×50 mL). The combined extracts were washed with a saturated aqueous NaCl solution, dried and evaporated. The residue was crystallized from ethyl acetate-hexane to afford 5.56 g (yield 98%) of the title product. Mp. 138°–143° C. (dec.).

NMR: $\delta^{CDCl_3}$ ppm 3.89 (3H, s), 6.52 (1H, s), 7.2 (15H, s).

Compounds IV-2, IV-3, IV-4', IV-5', IV-6' and IV-7' were prepared by the general procedure set forth above.

| Compound | R² (or R²') | Yield (%) | Mp (°C., dec.) | Literature Mp (°C., dec.) |
|---|---|---|---|---|
| IV-1 | methyl | 98 | 138–143 | ca. 140[1] |
| IV-2 | ethyl | 85 | 140–145 | not reported[1] |
| IV-3 | allyl | 66 | 170–178 | ca. 170[1] |
| IV-4' | —C(CH₃)₂COOtButyl | 77 | 174–175 | 152–156[2]; 190[3] |
| IV-5' | 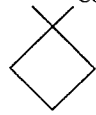 COOtButyl | 78 | 163–164 | not reported[3] |
| IV-6' | 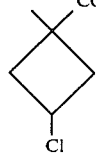 COOtButyl, Cl | 51 | 125–135 | new compound |
| IV-7 | —CH₂C≡CH | 88 | 136–138 | [4] |

[1]Tetrahedron, 34, 2233 (1978)
[2]U.S. Pat. No. 4,258,041
[3]U.S. Pat. No. 4,288,434
[4]The corresponding NH₂ compound is described in U.S. Pat. No. 4,294,960

PREPARATION NO. 3

Benzhydryl 3-Hydroxymethyl-7-phenylacetamido-3-cephem-4-carboxylate (VIII)

To a stirred suspension of phosphate buffer (pH 7, 162.5 mL) and wheat bran (20 g, dry) at room temperature was added 7-phenylacetamidocephalosporanic acid sodium salt (5 g, 12.1 mmoles) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 mL) followed by a 0.5M solution of diphenyldiazomethane in methylene chloride (24 mL). The pH was then adjusted to 3.0 with 28% phosphoric acid. After 1 hoour the reaction mixture was allowed to rise to 20° C. Heptane (56 mL) was slowly added and the resulting crystalline title product was recovered by filtration. Yield of the title product was 3.0 g (50%).

PREPARATION NO. 4

Benzhydryl 7-Amino-3-chloromethyl-3-cephem-4-carboxylate (V)

To a slurry of PCl₅ (8.3 g, 40 mmoles) in CH₂Cl₂ (100 mL) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate prepared in Preparation No. 3 (5.1 g, 10 mmoles) with stirring at −40° C., in one portion. The mixture was stirred at −10° C. for 15 minutes and allowed to stand at −10° C. to −15° C. for 7 hours. To the cooled solution (−20° C.) was added propane-1,3-diol (10 mL) and the mixture was allowed to stand at −20° C. for 16 hours and then at room temperature for 20 minutes with stirring. The resulting solution was washed with ice-water (2×20 mL) and saturated aqueous NaCl (10 mL), dried over MgSO₄ and concentrated in vacuo. The gummy residue (12 g) was dissolved in a mixture of CHCl₃ and n-hexane (2:1), and subjected to chromatography using a silica gel column (200 g) and the same solvent as eluant. Fractions containing the title compound were evaporated in vacuo and the residue triturated with n-hexane to give the title product (2.1 g, 51%), melting at >110° C. (dec.).

IR: $\nu_{KBr}$ 3400, 2800, 1785, 1725 cm⁻¹.

UV: $\lambda_{max}^{EtOH}$ 265 nm (E₁ cm¹% 160).

NMR: $\delta_{ppm}^{DMSO-d_6+CDCl_3}$ 3.69 (2H, s), 4.43 (2H, s), 5.09 (1H, d, J=4.5 Hz), 5.24 (1H, d, J=4.5 Hz), 6.87 (1H, s), 7.3 (10H, m).

PREPARATION NO. 5

Benzhydryl 3-Chloromethyl-7-[(Z)-2-methoxyimino-2-(2-tritylaminothiazol-4-yl)acetamido]-3-cephem-4-carboxylate (VI-1)

Benzhydryl 7-amino-3-chloromethyl-3-cephem-4-carboxylate prepared in Preparation No. 4 (2.29 g, 5.52 mmoles) in $CH_3CN$ (57 mL) was treated with bis(trimethylsilyl)acetamide (BSA, 4.09 mL, 16.6 mmoles) at room temperature for 50 minutes to give a clear solution. To the solution was added an acid chloride solution, which was prepared from (Z)-2-methoxyimino-2-(2-tritylaminothiazol-4-yl)acetic acid (IV-1) (2.04 g, 4.60 mmoles) and $PCl_5$ (1.15 g, 5.52 mmoles) in methylene chloride (20 mL). The mixture was stirred at room temperature for 30 minutes, poured into cold water (200 mL) and extracted with ethyl acetate ($3 \times 100$ mL). The combined extracts were washed with aqueous NaCl, dried and evaporated. The residual syrup (4 g) was chromatographed on a silica gel (150 g) column by eluting with 10:1 and 3:1 mixtures of toluene and ethyl acetate successively. The fractions containing the desired compound were combined and evaporated to afford 2.61 g (68%) of VI-1 as an amorphous powder.

NMR: $\delta^{CDCl_3}$ ppm 3.50 (2H, s), 4.02 (3H, s), 4.33 (2H, s), 4.98 (1H, d), 5.87 (1H, q), 6.65 (1H, s), 6.90 (1H, s), 7.3 (25H, m).

PREPARATION NO. 6

Benzhydryl 3-Iodomethyl-7-[(Z)-2-methoxyimino-2-(2-tritylaminothiazol-4-yl)acetamido]-3-cephem-4-carboxylate (VII-1)

A mixture of the 3-chloromethyl derivative prepared in Preparation No. 5 (VI-1) (1.50 g, 1.79 mmoles) and NaI (1.34 g, 8.93 mmoles) in methyl ethyl ketone (30 mL) was stirred at room temperature for 1 hour. After evaporation of the solvent the residue was dissolved in ethyl acetate (100 mL) and washed with water, aqueous $Na_2S_2O_3$ and aqueous NaCl, dried and evaporated to give the title compound VII-1 (1.47 g, 89%) as an amorphous powder.

NMR: $\delta^{CDCl_3}$ ppm 3.55 (2H, ABq), 4.00 (3H, s), 4.25 (2H, s), 4.97 (1H, d), 5.80 (1H, q), 6.65 (1H, s), 6.90 (1H, s), 7.3 (25H, m).

PREPARATION NO. 7

Benzhydryl 3-Chloromethyl-7-[(Z)-2-ethoxyimino-2-(2-tritylaminothiazol-4-yl)acetamido]-3-cephem-4-carboxylate (VI-2)

To a solution of (Z)-2-ethoxyimino-2-(2-tritylaminothiazol-4-yl)acetic acid (IV-2) (1.095 g, 2.4 mmoles) in dichloromethane (20 mL) was added phosphorus pentachloride (500 mg). After stirring for 1 hour at room temperature, the mixture was added in one portion to an ice-cooled solution of Compound V (1.083 g, 2.4 mmoles) and BSA (1 mL) in dichloromethane (20 mL). After stirring for 0.5 hour the reaction mixture was poured into 10% aqueous $NaHCO_3$ (200 mL) and extracted with $CHCl_3$ (100 mL). The extract was washed with water, dried over $MgSO_4$, and evaporated under reduced pressure. The residue was chromatographed on a silica gel column. Elution with $CHCl_3$ gave VI-2 as an amorphous powder, 1.76 g (86%).

NMR: $\delta^{CDCl_3}$ ppm 1.40 (3H, t, $CH_2CH_3$), 3.53 (2H, ABq, 2-H), 4.37 (2H, s, —$CH_2Cl$), 4.60 (2H, q, —$CH_2CH_3$), 4.90 (1H, d, 6-H), 5.89 (1H, d, 7-H), 6.88 (1H, s, thiazole-H), 6.91 (1H, s, benzhydryl-CH).

PREPARATION NO. 8

Diphenylmethyl 7-[(Z)-2-Ethoxyimino-2-(2-tritylaminothiazol-4-yl)acetamido]-3-iodomethyl-3-cephem-4-carboxylate (VII-2)

A mixture of VI-2 prepared in Preparation No. 7 (1.07 g, 1.25 mmoles) and NaI (562 mg, 2.75 mmoles) in acetone (20 mL) was stirred for 1 hour. The mixture was filtered and the filtrate was poured into water and extracted with ethyl acetate. The organic layer was washed successively with 5% aqueous $Na_2S_2O_3$, water and saturated aqueous NaCl, dried over $MgSO_4$ and evaporated to give 1.04 g (89%) of Compound VII-2.

NMR: $\delta^{CDCl_3}$ ppm 3.55 (2H, q, 2-H), 4.27 (2H, s, $CH_2I$), 5.02 (1H, d, 6-H), 5.87 (1H, d, 7-H), 6.68 (1H, s, thiazole ring H), 6.93 (1H, s, benzhydryl-CH).

PREPARATION NO. 9

Benzhydryl 7-[(Z)-2-Allyloxyimino-2-(2-tritylaminothiazol-4-yl)acetamido]-3-chloromethyl-3-cephem-4-carboxylate (VI-3)

To a suspension of Compound V (1.35 g, 3 mmoles) in methylene chloride (20 mL) was added BSA (1.1 mL, 4.5 mmoles), and the mixture was stirred for 30 minutes at room temperature to become a clear solution. A mixture of (Z)-2-allyloxyimino-2-(2-tritylaminothiazol-4-yl)acetic acid (IV-3) (1.40 g, 3.0 mmoles) and phosphorus pentachloride (690 mg, 3.3 mmoles) in methylene chloride (20 mL) was stirred for 15 minutes at room temperature and poured in one portion into the solution of the trimethylsilylated Compound V. The mixture was stirred for 20 minutes at room temperature and diluted with ethyl acetate (200 mL), washed with aqueous sodium bicarbonate and water, dried and evaporated under reduced pressure. The oily residue was purified by silica gel column chromatography (Wakogel, C-200, 30 g). The column was eluted with chloroform and the fractions containing the desired product were combined. Evaporation under reduced pressure afforded the title compound (VI-3) as an amorphous powder, yield 2.32 g (89%). Mp. 100°–115° C. (dec.).

IR: $\nu_{max}^{KBr}$ cm$^{-1}$ 3390, 1790, 1730, 1680, 1530, 1380, 1250, 1160, 1020.

NMR: $\delta^{CDCl_3}$ ppm 3.50 (2H, 2-H), 4.32 (2H, s, 3-$CH_2$), 4.6–6.1 (7H, m, $CH_2CH=CH_2$ and 6,7-H), 6.70 (1H, s, thiazole-H), 6.90 (1H, s, $Ph_2CH$), 7.1–7.6 (30H, m, phenyl protons).

Anal. Calc'd. for $C_{48}H_{40}N_5O_5S_2Cl \cdot \frac{1}{3}CHCl_3$: C, 64.05; H, 4.45; N, 7.73; S, 7.08; Cl, 7.82. Found: C, 64.13, 63.99; H, 4.61, 4.64; N, 7.50, 7.30; S, 6.85, 6.85; Cl, 7.55, 7.46.

PREPARATION NO. 10

Benzhydryl 7-[(Z)-2-Allyloxyimino-2-(2-tritylaminothiazol-4-yl)acetamido]-3-iodomethyl-3-cephem-4-carboxylate (VII-3)

A mixture of Compound VI-3 (2.30 g, 2.65 mmoles) and sodium iodide (2 g, 13.3 mmoles) in acetone (15 mL) was stirred for 1 hour at room temperature and then evaporated under reduced pressure. A solution of the oily residue in ethyl acetate (200 mL) was washed with 10% sodium thiosulfate and water, evaporated under reduced pressure to afford Compound VII-3 as an amorphous powder, which was used in the subsequent step without further purification. Yield 2.52 g (99%).

PREPARATION NO. 11

Benzhydryl 3-Chloromethyl-7-[(Z)-2-(2-t-butoxycarbonylprop-2-oxyimino)-2-(2-tritylaminothiazol-4-yl)acetamido]-3-cephem-4-carboxylate (VI-4')

Procedure 1

A mixture of (Z)-2-(2-t-butoxycarbonylprop-2-oxyimino)-2-(2-tritylaminothiazol-4-yl)acetic acid (IV-4') (1.94 g, 3.6 mmoles) DCC (742 mg, 3.6 mmoles) and N-hydroxybenztriazole (486 mg, 3.6 mmoles) in tetrahydrofuran (THF) (45 mL) was stirred at room temperature for 45 minutes, during which dicyclohexylurea separated. The dicyclohexylurea was removed by filtration and the filtrate was mixed with V (1.5 g, 3.6 mmoles). The mixture was stirred overnight at room temperature and then evaporated in vacuo. The residual oil was dissolved in $CHCl_3$ (20 mL), washed with saturated aqueous $NaHCO_3$ and saturated aqueous NaCl, dried over $MgSO_4$ and evaporated to dryness. The residue (3.9 g) was dissolved in n-hexane:$CHCl_3$ (1:2) and passed through a silica gel column (40 g) using the same solvent system. Fractions containing the title compound were evaporated in vacuo to give 1.3 g (39%) of VI-4' melting at >100° C. (dec.).

IR: $\nu_{max}^{KBr}$ cm$^{-1}$ 3390, 1790, 1715, 1690.

UV: $\lambda_{max}^{EtOH}$ nm 240 (E$_1$ $_{cm}^{1\%}$ 280), 265 (E$_1$ $_{cm}^{1\%}$ 190).

NMR: $\delta^{CDCl_3}$ ppm 1.45 (9H, s), 1.63 and 1.66 (6H, each s), 3.49 (2H, broad s), 4.34 (2H, s), 4.96 (1H, d, J=4.5 Hz), 5.90 (1H, d-d, J=4.5 and 7.5), 6.66 (1H, s), 6.86 (1H, s), 7.0–7.5 (25H, m), 8.23 (1H, d, J=7.5 Hz).

Procedure 2

A solution of V (1.86 g, 4.49 mmoles) in $CH_3CN$ (46.5 mL) was treated with BSA (3.33 mL, 13.5 mmoles) at room temperature for 50 minutes to give a clear solution. To the solution was added an acid chloride solution which had been prepared from IV-4' (2.56 g, 4.49 mmoles) and PCl$_5$ (1.12 g, 5.38 mmoles) in methylene chloride (26 mL). The mixture was stirred at room temperature for 30 minutes, poured into cold water (100 mL) and extracted with ethyl acetate (3×50 mL). The combined extracts were washed with aqueous NaCl, dried and evaporated. The residual syrup (5 g) was chromatographed on a silica gel (100 g) column by eluting with 10:1 mixture of toluene and ethyl acetate. The fractions containing the desired compound were combined and evaporated to afford 2.84 g (65%) of VI-4'.

PREPARATION NO. 12

Benzhydryl 7-[(Z)-2-(2-t-Butoxycarbonylprop-2-oxyimino)-2-(2-tritylaminothiazol-4-yl)acetamido]-3-iodomethyl-3-cephem-4-carboxylate (VII-4')

A mixture of VI-4' (500 mg, 0.53 mmole) and NaI (240 mg, 1.6 mmoles) in acetone (3 mL) was stirred for 2 hours at room temperature and then evaporated in vacuo. To the residue were added $CH_2Cl_2$ (20 mL) and water (10 mL). The organic layer was washed with 10% w/v sodium thiosulfate (5 mL) and aqueous NaCl (5 mL), dried over $MgSO_4$ and evaporated to dryness to give 540 mg (99%) of VII-4' as an amorphous powder melting at 106° C. (dec.).

IR: $\nu_{max}^{KBr}$ cm$^{-1}$ 3350, 1790, 1690.

UV: $\lambda_{max}^{EtOH}$ nm 240 (E$_1$ $_{cm}^{1\%}$ 270), 265 (E$_1$ $_{cm}^{1\%}$ 190).

NMR: $\delta^{CDCl_3}$ ppm 1.44 (9H, s), 1.65 (6H, s), 3.54 (2H, ABq), 4.28 (2H, s), 4.98 (1H, d, J=4.5 Hz), 5.85 (1H, d-d, J=4.5 and 7.5 Hz), 6.70 (1H, s), 6.90 (1H, s), 7.1–7.5 (25H, m).

PREPARATION NO. 13

Diphenylmethyl 7-[(Z)-2-(1-t-Butoxycarbonylcyclobut-1-oxyimino)-2-(2-tritylaminothiazol-4-yl)acetamido]-3-chloromethyl-3-cephem-4-carboxylate (VI-5')

Phosphorus pentachloride (1.46 g, 7 mmoles) was added to a suspension of (Z)-2-(1-t-butoxycarbonylcyclobut-1-oxyimino)-2-(2-tritylaminothiazol-4-yl)acetic acid [IV-5'] (4.09 g, 7 mmoles) in 70 mL of dry methylene chloride, and the mixture was stirred for 1 hour at room temperature. The acid chloride solution was added at −20° C. to a solution of silylated 7-ACA ester, which was prepared by adding BSA (5.6 mL, 21 mmoles) to a stirred suspension of benzhydryl 7-amino-3-chloromethyl-3-cephem-4-carboxylate hydrochloride [V] (3.16 g, 7 mmoles) in dry methylene chloride (70 mL). The mixture was stirred for 20 minutes at −10° C. and then at room temperature for 40 minutes. The reaction mixture was evaporated and diluted with ethyl acetate (300 mL), and the organic layer was washed with 5% aqueous sodium bicarbonate, water and a saturated sodium chloride solution. After drying over sodium sulfate, the solvent was evporated and the residue was purified by silica gel column chromatography (Wako gel C-200, 60 g); elution with chloroform. The fractions containing the desired product were combined and evaporated to obtain 5.88 g (86%) of VI-5' as a yellow powder.

IR: $\nu_{max}^{KBr}$ cm$^{-1}$ 1790, 1725, 1690, 1525.

UV: $\lambda_{max}^{EtOH}$ nm 240 (E$_1$ $_{cm}^{1\%}$=232), 265 (E$_1$ $_{cm}^{1\%}$=181).

PREPARATION NO. 14

Diphenylmethyl 7-[(Z)-2-(1-t-Butoxycarbonylcyclobut-1-oxyimino)-2-(2-tritylaminothiazol-4-yl)acetamido]-3-iodomethyl-3-cephem-4-carboxylate (VII-5')

To a stirred solution of VI-5' (5.4 g, 5.5 mmoles) in acetone (108 mL) was added sodium iodide (2.48 g, 16.5 mmoles), and the mixture was stirred at room temperature for 3 hours. The reaction mixture was then filtered and evaporated to dryness, and the residue was dissolved in ethyl acetate (200 mL). The solution was washed with water (100 mL), 10% w/v sodium thiosulfate (40 mL) and saturated sodium chloride (3×70 mL). After drying over magnesium sulfate, the solvent was removed under reduced pressure to give 5.38 g (91%) of VII-5' as a yellow powder.

IR: $\nu_{max}^{KBr}$ cm$^{-1}$ 1790, 1725, 1690, 1525.

UV: $\lambda_{max}^{EtOH}$ nm 240 (E$_1$ $_{cm}^{1\%}$=197), 265 (E$_1$ $_{cm}^{1\%}$=154).

NMR: $\delta^{CDCl_3}$ ppm 1.45 (9H, s), 1.8–2.8 (6H, m), 3.52 (2H, ABq), 4.25 (2H, s), 4.98 (1H, d, J=5.3 Hz), 5.87 (1H, dd, J=9 and 5.3 Hz), 6.70 (1H, s), 6.88 (1H, s), 6.90 (1H, s), 7.28 (25H, s), 8.41 (1H, d, J=9 Hz).

PREPARATION NO. 15

7-[2-(3-Chloro-1-t-butoxycarbonylcyclobut-1-oxyimino)-2-(2-tritylaminothiazol-4-yl)acetamido]cephalosporanic acid Phosphorus pentachloride (395 mg, 1.9 mmoles) was added to a solution of 2-(3-chloro-1-t-butoxycarbonyl-cyclobut-1-oxyimino)-2-(2-tritylaminothiazol-4-yl)acetic acid (IV-6') (1.0 g, 1.62 mmoles) in methylene chloride (6 mL) and the mixture was stirred for 1 hour at room temperature. N,O-Bistrimethylsilylacetamide (1.47 mL, 6 mmoles) was added to a suspension of 7-ACA (544 mg, 2 mmoles) in dry acetonitrile (15 mL) and the mixture was stirred for 20 minutes at room temperature to become a clear solution. To this solution was added dropwise the acid chloride solution, and the mixture was stirred for 1 hour at room temperature. The reaction mixture was evaporated under reduced pressure to remove the acetonitrile, diluted with ethyl acetate (300 mL), washed with water, dried and evaporated under reduced pressure. The residue was chromatographed on a column of silica gel (Wako-gel, C-200, 30 g) and was eluted with chloroform-methanol (100:1). The fractions containing the desired product were combined and evaporated under reduced pressure to afford the title product as an amorphous powder. Yield, 1.31 g (90%), mp. 120°–130° C. (dec.).

IR: $\nu_{max}^{KBr}$ cm$^{-1}$ 3400–2700, 1725, 1690, 1530, 1220.
UV: $\lambda_{max}^{EtOH}$ nm($\epsilon$) 245 (sh, 19600).
NMR: $\delta^{CDCl_3}$ ppm 1.44 (9H, s, t-Bu), 2.04 (3H, s, OAc), 2.7–3.5 (5H, m, 2-H, cyclobutane-H), 6.68 (1H, s, thiazole-H), 7.0–7.5 (15H, m, trityl-H).

Anal. Calc'd for $C_{43}H_{42}N_5O_9S_2Cl$: C, 59.20; H, 4.85; N, 7.03; s, 6.32. Found: C, 58.02; H, 4.62; N, 7.01; S, 6.32.

PREPARATION NO. 16

7-[2-(1-Carboxy-3-chlorocyclobut-1-oxyimino)-2-(2-aminothiazol-4-yl)]acetamidocephalosporanic acid [XX-6]

A mixture of the compound prepared in Preparation No. 15 (0.946 g, 1.08 mmoles) and trifluoroacetic acid (4 mL) was stirred for 1.5 hours at room temperature and diluted with diisopropyl ether (200 mL) to give a precipitate, which was collected by filtration. A suspension of the precipitate in water (20 mL) was extracted with ethyl acetate (3×100 mL). The combined extracts were washed with water, dried and evaporated under reduced pressure. The residue was triturated with ether and collected by filtration to give 264 mg (43%) of the title product [XX-6].

IR: $\nu_{max}^{nuj.}$ cm$^{-1}$ 1770, 1730, 1660, 1630, 1240.
NMR: $\delta^{D_2O}$ ppm 2.07 (3H, s, OAc), 2.7–3.0 (4H, m, cyclobutane-H), 3.50 (2H, d, 2-H), 5.15 (1H, d, 4 Hz, 6-H), 5.75 (1H, d, 4 Hz, 7-H), 6.92 (1H, s, thiazole-H).

PREPARATION NO. 17

Diphenylmethyl 3-chloromethyl-7-[(Z)-2-propargyloxyimino-2-(2-tritylaminothiazol-4-yl)acetamido]-3-cephem-4-carboxylate [VI-7]

Phosphorus pentachloride (910 mg) was added to a solution of (Z)-2-propargyloxyimino-2-(2-tritylaminothiazol-4-yl)acetic acid (IV-7) (1.7 g, 3.6 mmoles) in dichloromethane (30 mL). After stirring for 1 hour at room temperature the mixture was added in one portion to an ice-cooled solution of (V) (1.98 g, 4.4 mmoles) and N,O-bis(trimethylsilyl)acetamide (1.5 mL) in dichloromethane (30 mL). After stirring for 1 hour, the reaction mixture was poured into 10% aqueous NaHCO₃ (300 mL) and extracted with ethyl acetate (300 mL). The extract was washed with water, dried over MgSO₄ and evaporated under reduced pressure. The residue was chromatographed on a silica gel column. Elution with CHCl₃ gave the title compound "VI-7" as an amorphous powder weighing 2.1 g (66%).

NMR: $\delta^{CDCl_3}$ ppm 2.45 (1H, t, CH), 3.53 (2H, d, 2-CH₂), 4.37 (2H, s, —CH₂Cl), 4.83 (2H, d, O—CH₂C≡CH), 5.03 (1H, d, 6-H), 5.90 (1H, q, 7-H), 6.70 (1H, s, thiazole-H), 6.92 (1H, s, benzhydryl-CH).

PREPARATION NO. 18

Diphenylmethyl 7-[(Z)-2-propargyloxyimino-2-(2-tritylaminothiazol-4-yl)acetamido]-3-iodomethyl-3-cephem-4-carboxylate [VII-7]

A mixture of diphenylmethyl 3-chloromethyl-7-[(Z)-2-propargyloxyimino-2-(2-tritylaminothiazol-4-yl)acetamido]-3-cephem-4-carboxylate (VI-7) (2.0 g, 2.3 mmoles) and NaI (1.04 g, 6.9 mmoles) in acetone (40 mL) was stirred for 1 hour. The mixture was filtered and the filtrate was poured into water and extracted with ethyl acetate. The organic layer was washed with 5% aqueous Na₂S₂O₃, water and a saturated aqueous NaCl, successively. It was then dried over MgSO₄ and evaporated to give 2.2 g (98%) of the title compound [VII-7].

NMR: $\delta^{CDCl_3}$ ppm 2.45 (1H, t, CH), 3.53 (2H, d, 2-CH₂), 4.25 (2H, s, CH₂I), 4.83 (2H, d, O—CH₂), 5.0 (1H, d, 6-H), 5.80 (1H, q, 7-H), 6.70 (1H, s, thiazole-H), 6.92 (1H, s, benzhydryl-CH).

EXAMPLE 1

7-[(Z)-2-(2-Aminothiazol-4-yl)-2-(2-carboxyprop-2-oxyimino)acetamido]-3-(2-methylthiothiazolio)methyl-3-cephem-4-carboxylate [Ia]

Silver tetrafluoroborate (90% pure, 720 mg; 3.7 mmoles) was added to a solution of diphenylmethyl 7-[(Z)-2-(2-t-butoxycarbonylprop-2-oxyimino)-2-(2-tritylaminothiazol-4-yl)acetamido]-3-iodomethyl-3-cephem-4-carboxylate [VII-4'] (3.7 g 3.7 mmoles) and 2-methylthiothiazole (970 mg, 7.4 mmoles) in dry CH₂Cl₂ (40 mL) at −20° C., and the mixture was stirred at room temperature for 40 minutes. The reaction mixture was filtered and the filtrate was diluted with ether (80 mL) to separate 4.3 g of the precipitate, which was recovered by filtration and treated with a mixture of trifluoroacetic acid [TFA]](10 mL) and anisole (1 mL), with stirring, for 1 hour at room temperature. The mixture was filtered and the filter cake was washed with TFA (5 mL). The combined TFA solution was concentrated to a small volume and diluted with ether (100 mL) to give the TFA salt of Ia (2.57 g), which was collected by filtration, washed with ether (20 mL) and dried under reduced pressure. To a solution of the TFA salt (2.45 g) in methanol (20 mL) was added a solution of 1M sodium 2-ethylhexanoate in ethyl acetate (4mL). The mixture was stirred for 15 minutes at room temperature and additional ethyl acetate was added to precipitate the crude product (1.7 g), which was collected by filtration and dried in vacuo. The product (1.6 g) was dissolved in water by adjusting the pH to 6.9 with NaHCO₃ and purified by preparative HPLC (Waters Associates, System 500, PrepPAK 500/C₁₈, 4.8%

CH₃OH) to afford 685 mg (41%) of the title compound [Ia]. Estimated purity 85% (by HPLC). Mp 140° C. (dec.).

IR: $\nu_{max}^{KBr}$ cm⁻¹ 1770, 1660, 1600, 1400.

UV: $\lambda_{max}^{Phosphate\ buffer\ pH\ 7}$ nm($\epsilon$) 236(18000), 260(17000), 280(17000).

NMR: $\delta^{D2O}$ ppm 1.63 (6H, s, C—CH₃), 3.10 (3H, s, S—CH₃), 3.35 and 3.65 (each 1H, d, J=16, 2-H), 5.35 (3H, m, 6-H and 3-CH₂), 5.95 (1H, d, J=5, 7-H), 7.06 (1H, s, thiazole-H), 7.97 (1H, d, J=4, thiazole-H), 8.22 (1H, d, J=4, thiazole-H).

EXAMPLE 2

7-[(Z)-2-(2-Aminothiazol-4-yl)-2-(1-carboxycyclobut-1-oxyimino)acetamido]-3-(2-methylthiothiazolio)methyl-3-cephem-4-carboxylate [Ib]

To a mixture of diphenylmethyl 7-[(Z)-2-(1-t-butoxycarbonylcyclobut-1-oxyimino)-2-(2-tritylaminothiazol-4-yl)acetamido]-3-iodomethyl-3-cephem-4-carboxylate [VII-5'] (4.3 g, 4 mmoles) and 2-methylthiothiazole (1.05 g, 8 mmoles) in dry CH₂Cl₂ (40 mL) was added silver tetrafluoroborate (90% pure, 867 mg, 4 mmoles) at −20° C. The mixture was stirred at ambient temperature for 1.5 hours and filtered through a dicalite pad. The filtrate was evaporated in vacuo and the residual oil was triturated with ethyl ether (80 mL) to give 4.48 g of the protected intermediate, which was treated with TFA (20 mL) in the presence of anisole (2 mL) at room temperature for 1 hour. The mixture was filtered and the insolubles were washed with TFA. The filtrate and the washings were combined and evaporated to give an oily residue, which was triturated with ethyl ether (100 mL) to afford 2.38 g of the TFA salt of Ib. To a suspension of the TFA salt (2.18 g) in CH₃OH (20 mL) was added a solution of 1M sodium 2-ethylhexanoate in ethyl acetate (15 mL). After stirring at room temperature for 30 minutes, the mixture was diluted with ethyl acetate (100 mL) to give crude Ib (1.98 g). The product (1.48 g) was purified by preparative HPLC (Waters Associates, System 500, PrepPAK 500/C₁₈, 8% CH₃OH) to afford 635 mg of the title product. Repeating chromatography of the above sample (350 mg) by eluting with H₂O—CH₂OH (200:10) gave 248 mg (27%) of the title product [Ib], as a light-yellow amorphous powder. Estimated purity 85% (by HPLC). Mp 165° C. (dec.).

IR: $\nu_{max}^{KBr}$ cm⁻¹ 1765, 1660, 1600, 1395.

UV: $\lambda_{max}^{Phosphate\ buffer\ pH\ 7}$ nm($\epsilon$) 240(17200), 260(17700), 280(18000).

NMR: $\delta^{D2O}$ ppm 1.25–2.75 (6H, m, cyclobutane-H), 3.09 (3H, s, S—CH₃), 3.34 and 3.67 (each 1H, d, J=18, 2-H), 5.35 (3H, m, 3-CH₂ and 6-H), 5.97 (1H, d, J=5, 7-H), 7.09 (1H, s, thiazole-H), 7.98 and 8.23 (each 1H, d, J=4, thiazole-H).

EXAMPLE 3

7-[(Z)-2-(2-Aminothiazol-4-yl)-2-(methoxyimino)acetamido]-3-(2-methylthiothiazolio)methyl-3-cephem-4-carboxylate [Ic]

To a solution of diphenylmethyl 7-[(Z)-2-methoxyimino-2-(2-tritylaminothiazol-4-yl)acetamido]-3-iodomethyl-3-cephem-4-carboxylate [VII-1] (3.72 g, 4 mmoles) and 2-methylthiothiazole (1.05 g, 8 mmoles) in dry CH₂Cl₂ (40 ml) was added silver tetrafluoroborate (90% pure, 867 mg, 4 mmoles) at −20° C. The mixture was stirred at room temperature for 2 hours and filtered through a dicalite pad. The filtrate was evaporated and the oily residue was triturated with ethyl ether (80 mL) to give 4.02 g of the N-tritylated benzhydryl ester, which was treated with TFA (20 mL) and anisole (2 mL), and stirred at room temperature for 1 hour. The mixture was filtered and insolubles were washed with TFA (5 mL). The filtrate and the washings were combined and concentrated to yield an oil, which was triturated with ethyl ether (100 mL) to give 2.24 g of the crude TFA salt of Ic. To a suspension of the TFA salt (2.14 g) in CH₃OH (20 mL) was added a solutin of 1M sodium 2-ethylhexanoate in ethyl acetate (12 mL). The mixture was stirred at room temperature for 30 minutes, then concentrated in vacuo and diluted with ethyl acetate (100 mL) to precipitate 1.71 g of crude Ic. A suspension of the crude product (1.6 g) in water (20 mL) was adjusted to pH 7.4 with NaHCO₃ and chromatographed by preparative HPLC (Waters Associates, System 500, PrepPAK 500/C₁₈, 20% CH₃OH) to yield 610 mg of Ic. Estimated purity 60% (by HPLC).

The above sample (540 mg) was further purified by HPLC (Lichrosorb RP-18, 8×300 mm), eluting with 0.01M ammonium phosphate buffer solution (pH 7.2) containing 20% CH₃OH. The fractions containing the desired product were combined and concentrated to ca. 1 mL. The concentrate was re-chromatographed with the same column packing and eluted with 20% aqueous CH₃OH. The fractions containing the desired material were combined, concentrated and lyophilized to yield 223 mg of the title compound [Ic] (13.5% from VII-1) as a light-yellow amorphous powder. Estimated purity 75% (by HPLC). Mp>160° C. (dec.).

IR: $\nu_{max}^{KBr}$ cm⁻¹ 1770, 1650, 1605, 1390.

UV: $\lambda_{max}^{Phosphate\ buffer\ pH\ 7}$ nm($\epsilon$) 235(18700), 260(17900), 280(17600).

NMR: $\delta^{D2O}$ ppm 3.08 (3H, s, S—CH₃), 3.33 and 3.64 (each 1H, d, J=18, 2-H), 4.10 (3H, s, OCH₃), 5.33 (3H, m, 3-CH₂ and 6-H), 5.93 (1H, d, J=5, 7-H), 7.05 (1H, s, thiazole-H), 7.95 and 8.20 (each 1H, d, J=4, thiazole-H).

EXAMPLE 4

7-[(Z)-2-(2-Aminothiazol-4-yl)-2-(ethoxyimino)acetamido]-3-(2-methylthiothiazolio)methyl-3-cephem-4-carboxylate [Id]

To an ice-cooled solution of diphenylmethyl 7-[(Z)-2-(ethoxyimino)-2-(2-tritylaminothiazol-4-yl)acetamido]-3-iodomethyl-3-cephem-4-carboxylate [VII-2] (517 mg, 0.55 mmole) and 2-methylthiothiazole (85.3 mg, 0.65 mmole) in CH₂Cl₂ (10 ml) was added AgBF₄ (117 mg, 0.60 mmole) and the mixture was stirred for 1.5 hours at room temperature. The reaction mixture was diluted with CHCl₃ (100 mL), and the resulting precipitate was recovered by filtration and washed with CHCl₃ (100 mL). The filtrate and the washings were combined and washed with water, dried over MgSO₄ and evaporated. The residue was triturated with ether (50 mL) to give an amorphous solid (433 mg), which was dissolved in 90% TFA. The mixture was allowed to stand for 45 minutes at room temperature and then evaporated in vacuo at 10° C. The residue was triturated with ether to give crude Id (291 mg) which was dissolved in a small amount of methanol and passed through an HP-20 (20 mL) column by eluting with 30% aqueous methanol, to give 63.3 mg (29%) of the title compound [Id]. Estimated purity 70%.

IR: $\nu_{max}^{KBr}$ cm⁻¹ 1775, 1660, 1610, 1390.

UV: $\lambda_{max}^{Phosphate\ buffer\ pH\ 7}$ nm($\epsilon$) 235(19000), 260(17000), 280(16700).

NMR: $\delta^{D2O}$ ppm 1.41 (3H, t, J=7.5, OCH$_2$CH$_3$), 3.08 (3H, s, S—CH$_3$), 5.32 (1H, d, J=5.0, 6-H), 5.94 (1H, d, J=5.0, 7-H), 7.06 (1H, s, thiazole-H), 7.95 (1H, d, J=4.0, thiazole-H), 8.20 (1H, d, J=4, thiazole-H).

EXAMPLE 5

7-[(Z)-2-(2-Aminothiazol-4-yl)-2-(2-carboxyprop-2-oxyimino)acetamido]-3-thiazoliomethyl-3-cephem-4-carboxylate (Ie)

A solution of sodium 7-[(Z)-2-(2-aminothiazol-4-yl)-2-(2-carboxyprop-2-oxyimino)acetamido]cephalosporanate [XX-4] (571 mg, 1 mmole) and thiazole (160 mg, 1.9 mmoles) in water (1 ml) was adjusted to pH 7 with dilute hydrochloric acid. Potassium thiocyanate (5 g) was added and the mixture was heated at 80° C. for 1 hour. The reaction mixture was diluted with water (20 ml), acidified to pH 1 with dilute HCl and filtered to remove insolubles. The filtrate was chromatographed on a column of HP-20 (1.9×18 cm), and the column was eluted with water (1 L) and then with 30% aqueous methanol (1 L). The eluate was monitored by UV absorption at 260 nm. Methanolic fractions containing the desired product were combined and evaporated under reduced pressure. The residue was freeze-dried to afford the crude product (163 mg) as an amorphous powder, which was purified by HPLC (column, Lichrosorb RP-18, 0.8×30 cm; mobile phase, 0.01M NH$_4$H$_2$PO$_4$ buffer [pH 7.2]:CH$_3$OH=95:5). Th eluate was acidifed to pH 1 with dilute HCl and chromatographed on a column of HP-20 (1.9×10 cm). The column was eluted with water (1 L) and then with 30% aqueous methanol (0.5 L). Fractions containing the desired product were concentrated under reduced pressure. The residue was freeze-dried to give 51 mg (9.2%) of the title compound [Ie] as an amorphous powder. Mp>190° C. (gradually decomposed).

IR: $\lambda_{max}^{KBr}$ 3600–3000, 1775, 1660, 1610, 1530 cm$^{-1}$.
UV: $\lambda_{max}^{pH\ 7\ buffer}$ 238 nm ($\epsilon$ 20,800).
NMR: $\delta_{ppm}^{D2O+NaHCO3}$ 1.47 (6H, s, CH$_3$), 5.23 (1H, d, 4 Hz, 6-H), 5.82 (1H, d, 4 Hz, 7-H), 6.94 (1H, s, thiazole-H), 8.15 (1H, d, 4 Hz, thiazole-H), 8.38 (1H, d, 4 Hz, thiazole-H).

EXAMPLE 6

7-[(Z)-2-(2-Aminothiazol-4-yl)-2-(2-carboxyprop-2-oxyimino)acetamido]-3-[5-(2-hydroxyethyl)-4-methyl-thiazolio]methyl-3-cephem-4-carboxylate (If)

A solution of sodium 7-[(Z)-2-(2-aminothiazol-4-yl)-2-(2-carboxyprop-2-oxyimino)acetamido]-cephalosporanate [XX-4] (571 mg, 1 mmole) and 5-(2-hydroxyethyl)-4-methylthiazole (Tokyo-Kasei, 572 mg, 1 mmole) were reacted by the procedure described in Example 5. Workup of the reaction mixture was as described in Example 5, except that the mobile phase utilized for the HPLC was 0.01M NH$_4$H$_2$PO$_4$ buffer [pH 7.2]:CH$_3$OH=85:15. The yield of the title compound [If] was 83 mg (1.36%). Mp>190° C. (gradual decomp.).

IR: $\nu_{max}^{KBr}$ 3600–3000, 1770, 1660, 1610, 1530, 1160 cm$^{-1}$.
UV: $\lambda_{max}^{pH\ 7\ buffer}$ 240 nm(sh) ($\epsilon$ 18,000), 258 nm ($\epsilon$ 20,400).
NMR: $\delta_{ppm}^{DMSO-d6}$ 1.44 (6H, s, CH$_3$), 5.05 (1H, d, 5 Hz, 6-H), 5.28 (2H, br, 3-CH$_2$), 5.74 (1H, d-d, 5 and 8 Hz, 7-H), 6.68 (1H, s, thiazole-H), 7.20 (2H, br, NH$_2$), 9.27 (1H, d, 8 Hz, 7-NHCO), 10.17 (1H, s, thiazole-H).

EXAMPLE 7

7-[(Z)-2-(2-Aminothiazol-4-yl)-2-(2-carboxyprop-2-oxyimino)acetamido]-3-(4-methylthiazolio)methyl-3-cephem-4-carboxylate [Ig]

A solution of sodium 7-[(Z)-2-(2-aminothiazol-4-yl)-2-(2-carboxyprop-2-oxyimino)acetamido]cephalosporanate [XX-4] (1.02 g, 1.78 mmoles) and 4-methylthiazole (590 mg, 6 mmoles) were reacted by the procedure described in Example 5. Workup of the reaction mixture was as described in Example 5 except that the mobile phase utilized for the HPLC was 0.01M NH$_4$H$_2$PO$_4$ buffer [pH 7.2]:CH$_3$OH=90:10. The yield of the title product [Ig] was 44 mg (4.4%). Mp>190° C. (gradual decomposition).

IR: $\nu_{max}^{KBr}$ 3600–3000, 1770, 1660, 1610, 1535, 1360, 1160 cm$^{-1}$.
UV: $\lambda_{max}^{pH\ 7\ buffer}$ 250 nm ($\epsilon$ 18,900).
NMR: $\delta_{ppm}^{DMSO-d6}$ 1.45 (6H, s, CH$_3$), 5.05 (1H, d, 4 Hz, 6-H), 5.27 (2H, s, 3-CH$_2$), 5.70 (1H, d-d, 4 and 8 Hz, 7-H), 6.67 (1H, s, thiazole-H), 7.20 (2H, s, NH$_2$), 7.95 (1H, s, thiazole-H), 9.30 (1H, d, 8 Hz, CONH), 10.32 (1H, s, thiazole-H).

EXAMPLE 8

7-[(Z)-2-(2-Aminothiazol-4-yl)-2-(2-carboxyprop-2-oxyimino)acetamido]-3-(2-amino-3-thiazolio)methyl-3-cephem-4-carboxylate [Ih]

A mixture of 310 mg (0.59 mmole) of 7-[α-(2-aminothiazol-4-yl)-α-(2-carboxyprop-2-oxyimino)acetamido]-cephalosporanic acid [XX-4], 110 mg (1.10 mmoles) of 2-aminothiazole (commercially available) and 5 g of potassium thiocyanate in 1 ml of water was adjusted to pH 6.5 with 1N HCl and heated at 80° C. for 80 minutes. The reaction mixture was diluted with 10 ml of water and acidified (pH 1) with 6N HCl. The aqueous solution was chromatographed on a column of HP-20 (1.6×10 cm), and the column was eluted with H$_2$O (300 ml), 10% CH$_3$OH—H$_2$O (300 ml), 20% CH$_3$OH—H$_2$O (600 ml) and 50% CH$_3$OH—H$_2$O, successively. The eluate of 30% aqueous CH$_3$OH was concentrated under reduced pressure and lyophilized to give the crude product. The crude product was purified by HPLC (column, Lichrosorb RP-18, 0.4×30 cm, mobile phase 15% CH$_3$OH-phosphate buffer (pH 7)) and desalted by using an HP-20 column. Yield of the title product [Ih] was 36 mg (11%).

IR: $\nu_{max}^{KBr}$ cm$^{-1}$ 3300, 1770, 1610.
UV: $\lambda_{max}^{pH\ 7\ buffer}$ nm($\epsilon$) 245 (20500).
NMR: $\delta^{D2O}$ ppm 1.56 (6H, s), 3.17 (1H, d, J=18 Hz), 3.77 (1H, d, J=18 Hz), 5.2 (2H, m), 5.3 (1H, d, J=5 Hz), 5.90 (1H, d, J=5 Hz), 6.91 (1H, d, J=5 Hz), 7.05 (1H, s), 7.32 (1H, d, J=5 Hz).

EXAMPLE 9

7-[(Z)-2-(2-Aminothiazol-4-yl)-2-(2-carboxyprop-2-oxyimino)acetamido]-3-(5-methoxy-4-methylthiazolio)-methyl-3-cephem-4-carboxylate [Ii]

Silver tetrafluoroborate (100 mg, 0.5 mmole) was added to a mixture of diphenylmethyl 7-[(Z)-2-(2-t-butoxycarbonylprop-2-oxyimino)-2-(2-tritylamino-thiazol-4-yl)acetamido]-3-iodomethyl-3-cephem-4-carboxylate (VII-4') (577 mg, 0.5 mmole) and 5-methoxy-4-methylthiazole (146 mg, 1 mmole) [prepared according to the procedure described by D. S. Tarbell et al., J. Am. Chem. Soc., 72, 3138 (1950)] in methylene chloride (50 ml). The mixture was stirred for 20 minutes at room temperature and filtered. The filtrate was washed with water, evaporated under reduced pressure and the residue was triturated with ether to give the quaternized salt, which was collected by filtration (yield, 475 mg). The quaternized product was dissolved in cold TFA (2 ml), stirred for 1 hour at room temperature and evaporated under reduced pressure below 30° C., and the residue was triturated with ether. The crude TFA salt was collected by filtration (yield, 281 mg) and purified by HPLC (Column: Lichrosorb RP-18, Solvent: 0.01M $NH_4H_2PO_4$ (pH 7):$CH_3OH$=85:15). The fractions containing the desired compound were combined and concentrated under reduced pressure below 30° C. The concentrate was acidified to pH 2 (dilute HCl), chromatographed on a column of HP-20 (1.3×10 cm) and eluted with water and then with water-methanol (1:1). The fractions containing the desired product were combined, evaporated under reduced pressure and freeze-dried to give the title compound [Ii] as an amorphous powder. Yield, 61 mg (20%).

Estimated purity 90% (by HPLC).

IR: $\nu_{max}^{KBr}$ cm$^{-1}$ 3600–2000, 1770, 1660, 1600, 1535.

UV: $\lambda_{max}^{Phosphate\ buffer\ (pH\ 7)}$ nm($\epsilon$) 236 (17600), 258(sh) (16800).

NMR: $\delta^{D_2O+NaHCO_3}$ ppm 1.50 (6H, s, $CH_3$), 2.36 (3H, s, $CH_3$), 4.10 (3H, s, $OCH_3$), 5.1–5.4 (3H, m, 6-H, 3-$CH_2$), 5.75 (1H, d, J=4, 7-H), 6.95 (1H, s, thiazole-H).

EXAMPLE 10

7-[(Z)-2-(2-Aminothiazol-4-yl)-2-methoxyiminoacetamido]-3-[5-(2-aminoethyl)-4-methylthiazolio]methyl-3-cephem-4-carboxylate [Ij]

A mixture of diphenylmethyl 7-[(Z)-2-methoxyimino-2-(2-tritylaminothiazol-4-yl)acetamido]-3-iodomethyl-3-cephem-4-carboxylate (VII-1) 468 mg, 0.5 mmole) and 5-(2-t-butoxycarbonylaminoethyl)-4-methylthiazole (242 mg, 1 mmole) [prepared by t-butoxycarbonylation of 5-(2-aminoethyl)-4-methylthiazole; see K. M. Muravéva and M. N. Shchukina, Zh. Obshch. Khim., 33, 3723 (1963); CA, 60, 8012a (1964)] in a mixture of methylene chloride (2 mL) and DMSO (0.5 mL) was stirred for 6 hours at room temperature and diluted with ethyl acetate (100 mL). The mixture was washed with water and evaporated under reduced pressure. The residue was triturated with ether and 400 mg of the quaternary salt was collected by filtration and treated with TFA (5 mL) for 2 hours at room temperature. After removal of TFA under reduced pressure below 20° C., the mixtrue was triturated with ether and 310 mg of the TFA salt of the crude product was collected by filtration. The TFA salt was dissolved in a small amount of aqueous $NaHCO_3$ and chromatographed on a column of HP-20 (1.8×20 cm) by eluting with water. The fractions containing the title compound were combined, concentrated under reduced pressure and freeze-dried to give 36 mg (yield 14%) of the title product [Ij]. Estimated purity 50% (by HPLC).

IR: $\nu_{max}^{KBr}$ cm$^{-1}$ 3600–3200, 1770, 1660, 1530, 1350.

UV: $\lambda_{max}^{phosphate\ buffer\ (pH\ 7)}$ nm($\epsilon$) 232 (14600), 253 (14600).

NMR: $\delta^{D_2O}$ ppm 2.62 (3H, s, $CH_3$), 3.45 (4H, s, $CH_2$), 4.10 (3H, s, $OCH_3$), 5.94 (1H, d, 4 Hz, 7-H), 7.0 (1H, s, thiazole-H).

EXAMPLE 11

7-[(Z)-2-(2-Aminothiazol-4-yl)-2-(1-carboxycyclobut-1-oxyimino)acetamido]-3-(2-methylthiazolio)methyl-3-cephem-4-carboxylate [Ik]

Silver tetrafluoroborate (90% pure, 108 mg, 0.5 mmole) was added to a cold $CH_2Cl_2$ solution of benzhydryl 7-[(Z)-2-(1-t-butoxycarbonylcyclobut-1-oxyimino)-2-(2-tritylaminothiazol-4-yl)acetamido]-3-iodomethyl-3-cephem-4-carboxylate (VII-5′) (536 mg, 0.5 mmole) and 2-methylthiazole (99.2 mg, 1 mmole) [prepared by the procedure described by H. Erlenmyer, et al., Helv. Chim. Acta, 31, 1142 (1948)], and the mixture was stirred at room temperature for 2 hours. After filtration, the filtrate was concentrated to give an oily residue. The residue was triturated with ether (40 mL) to give amorphous powder (544 mg), which was mixed with TFA (2.5 mL) and anisole (0.25 mL). The mixture was stirred at ambient temperature for 30 minutes and filtered through a dicalite pad. The filter cake was washed with TFA, and the combined filtrate and wash were concentrated in vacuo. The residual oil was triturated with ether (40 mL) to give the TFA salt (240 mg) of the title compound. To a suspension of the salt (235 mg) in dry $CH_3OH$ (1 mL) was added a solution of 1M sodium 2-ethylhexanoate in ethyl acetate (1.6 mL), and the mixture was stirred at room temperature for 30 minutes. The mixture was diluted with ethyl acetate (20 mL) to give 215 mg of amorphous precipitate. The precipitate (205 mg) was dissolved in water (2 mL), and passed through an HP-20 (30 mL) column by eluting with water, 10% $CH_3OH$ and 30% $CH_3OH$ successively, to give 95 mg of the crude product, which was purified by HPLC eluting with 5% aqueous methanol to yield 14.5 mg of the title compound [Ik]. Estimated purity 70% (by HPLC).

IR: $\nu_{max}^{KBr}$ cm$^{-1}$ 1765, 1600(br), 1535, 1395.

UV: $\lambda_{max}^{Phosphate\ buffer\ (pH\ 7)}$ nm($\epsilon$) 243 (19000), 305 (6180).

NMR: $\delta^{D_2O}$ ppm 1.7–2.8 (6H, m, cyclobutane-H), 3.05 (3H, s, thiazole-2-$CH_3$), 3.28 and 3.68 (each 1H, d, J=18, 2-H), 5.35 (3H, m, 3-$CH_2$ and 6-H), 5.93 (1H, d, J=5, 7-H), 7.05 (1H, s, thiazole-H), 7.98 and 8.23 (each 1H, d, J=4, thiazole-H).

EXAMPLE 12

7-[(Z)-2-(2-Aminothiazol-4-yl)-2-(1-carboxycyclobut-1-oxyimino)acetamido]-3-(2-ethylthiothiazolio)methyl-3-cephem-4-carboxylate [Im]

To a mixture of benzhydryl 7-[(Z)-2-(1-t-butoxycarbonylcyclobut-1-oxyimino)-2-(tritylaminothiazol-4-yl)acetamido]-3-iodomethyl-3-cephem-4-carboxylate (VII-5′) (536 mg, 0.5 mmole) and 2-ethylthiothiazole (145 mg, 1 mmole) [prepared according to the procedure described by P. Bastianelli, et al., Bull. Soc. Chim. Fr., 1967 (1948)] in dry $CH_2Cl_2$ (5 mL) was added silver tetrafluoroborate (90% pure, 108 mg, 0.5 mmole) at −20° C. The mixture was stirred at room temperature for 1 hour and filtered through a dicalite pad. The filtrate was evaporated under reduced pressure and the oily residue was triturated with ether (30 mL) to give an amorphous precipitate (XIII) (586 mg), which was treated with TFA (2.8 mL) in the presence of anisole (0.28 mL) at ambient temperature for 30 minutes. The mixture was filtered and the filter cake was washed with TFA. The filtrate and the wash were combined and evaporated to yield an oily residue, which was triturated with ether (30 mL) to afford the TFA salt (350 mg) of the title compound. To a suspension of the TFA salt (330 mg) in dry CH$_3$OH (1 mL) was added a solution of 1M sodium 2-ethylhexanoate in ethyl acetate (1.8 mL). The mixture was stirred at room temperature for 30 minutes and diluted with ethyl acetate (20 mL) to give the crude product (296 mg). The precipitate (285 mg) was chromatographed on an HP-20 (60 mL) column by eluting with water, 10% aqueous methanol and 30% aqueous methanol, successively, to yield 99 mg of the solid material. This material (85 mg) was further purified by HPLC (Column: Lichrosorb RP-18, 8×300 mm) eluting with 15% aqueous methanol to afford 20 mg of the title compound [Im]. Estimated purity 80% (by HPLC).

IR: $\nu_{max}^{KBr}$ cm$^{-1}$ 1765, 1600(sh), 1535, 1395.

UV: $\lambda_{max}^{Phosphate\ buffer\ (pH\ 7)}$ nm($\epsilon$) 254 (17000), 285(sh) (16300).

NMR: $\delta^{D2O}$ ppm 1.62 (3H, t, J=7, CH$_3$CH$_2$S), 1.75–2.85 (6H, m, cyclobutane-H), 3.29 and 3.62 (each 1H, d, J=8, 2-H), 3.54 (2H, q, J=7, CH$_3$CH$_2$S), 5.32 (1H, d, J=5, 6-H), 5.93 (1H, d, J=5, 7-H), 7.05 (1H, s, thiazole-3-H), 7.93 and 8.18 (each 1H, d, J=4, thiazole-H).

EXAMPLE 13

7-[(Z)-2-(2-Aminothiazol-4-yl)-2-(2-carboxyprop-2-oxyimino)acetamido]-3-(2-carboxymethylthiothiazolio)methyl-3-cephem-4-carboxylate [In]

To a mixture of 2-(carboxymethylthio)thiazole (350 mg, 2 mmoles) and N,O-bistrimethylsilylacetamide (1 mL) in CH$_2$Cl$_2$ (10 mL) was added diphenylmethyl 7-[(Z)-2-(2-t-butoxycarbonylprop-2-oxyimino)-2-(2-tritylaminothiazol-4-yl)acetamido]-3-iodomethyl-4-carboxylate (VII-4') (1.06 g, 1 mmole). Silver tetrafluoroborate (200 mg, 1 mmole) was added to the solution at −30° C. with stirring. The mixture was stirred for 1 hour at room temperature and filtered to remove insolubles. The filtrate was concentrated to a small volume and diluted with ether (20 mL) to give a precipitate which was collected by filtration. The dried solid (1 g) was added to TFA (3 mL) containing anisol (1 drop). After 1 hour stirring at room temperature, the mixture was filtered and the filtrate was diluted with ether (20 mL). The separated solid (500 mg) was collected by filtration, dissolved in water (10 ml), adjusted to pH 5 by adding NaHCO$_3$ and purified on a PrepPAK 500/C$_{18}$ (150 mL) column using water as eluant. Fractions containing the title compound were evaporated in vacuo to give 49 mg (7.8%) of the title product [In] melting at 190° C. (dec.).

IR: $\nu_{max}^{KBr}$ cm$^{-1}$ 3400, 1760, 1660, 1600.

UV: $\lambda_{max}^{Phosphate\ buffer\ (pH\ 7)}$ nm(E$_1$ $_{cm}$$^{1\%}$) 235 (258), 260 (225), 285 (208).

NMR: $\delta^{DMSO-d6}$ ppm 1.4 (6H, s, C—CH$_3$), 4.0 (2H, s, CH$_2$CO), 4.98 (1H, d, J=4.5, 6-H), 5.10 (2H, s-br, 3-CH$_2$), 5.70 (1H, d-d, J=4.5 and 7.5, 7-H), 6.66 (1H, s, thiazole-H), 7.87 and 8.64 (each 1H, d, J=4, thiazole-H).

EXAMPLE 14

7-[2-(Z)-(2-Aminothiazol-4-yl)-2-(2-carboxyprop-2-yloxyimino)acetamido]-3-(2-formylaminothiazolio)-methyl-3-cephem-4-carboxylate [Io]

Silver tetrafluoroborate (195 mg, 1 mmole) was added to a stirred solution of VII-4' (1.06 g, 1 mmole) and 2-formylaminothiazole (260 mg, 2 mmoles) [prepared according to the procedure described by K. Takatori and S. Asano, Yakugaku Zasshi 80, 789 (1960)] in CH$_2$Cl$_2$ (20 mL) at −20° C., and the mixture was stirred at room temperature for 1.5 hours. The reaction mixture was filtered and the filtrate was washed with water (10 mL), dried over MgSO$_4$ and concentrated to a small volume. The concentrate was purified on silica gel (40 g) using CHCl$_3$ as eluant. Fractions containing the desired compound were evaporated to give 370 mg (35%) of the cephalosporin (XIII) melting at 125° C. (dec.).

IR: $\nu_{max}^{KBr}$ cm$^{-1}$ 3400, 1775, 1720, 1650.

UV: $\lambda_{max}^{EtOH}$ nm($\epsilon$) 245 (26000), 265 (20000), 271 (18000), 306 (16000).

NMR: $\delta^{DMSO-d6}$ ppm 1.4 (15H, s, CCH$_3$), 4.82 and 5.36 (each 1H, d, J=16, 3-CH$_2$), 5.18 (1H, d, J=4.5, 6-H), 5.78 (1H, d-d, J=4.5 and 7.5, 7-H), 6.66 (1H, s, thiazole-H), 5.8–7.6 (28H, m, phenyl-H, CH-phenyl and thiazole-H), 8.51 (1H, s, CHO), 8.71 (1H, s-br, N-H), 9.24 (1H, d, J=7.5, 7-NH).

A mixture of XIII (300 mg, 0.8 mmole), TFA (3 mL) and anisole (1 drop) was stirred for 1 hour at room temperature. The mixture was filtered and the filtrate was concentrated to a small volume. The concentrate was diluted with ether (50 mL) to separate an amorphous precipitate, which was collected by filtration and dried to give 180 mg of the crude product. To a suspension of the crude product (120 mg) in methanol (2 mL) was added a solution of M sodium 2-ethylhexanoate in ethyl acetate (0.5 mL). The mixture was stirred for 15 minutes and diluted with ethyl acetate (20 mL) to separate a precipitate (110 mg), which was dissolved in water and purified by column chromatography (Prep-PAK/C$_{18}$) using water as an eluant. Fractions containing the desired compound were combined and evaporated to dryness to give 55 mg (47%) of the title compound [Io] melting at 220° C. (dec.).

IR: $\nu_{max}^{KBr}$ cm$^{-1}$ 3300, 1760, 1660, 1595.

UV: $\lambda_{max}^{Phosphate\ buffer\ (pH\ 7)}$ nm(E$_1$ $_{cm}$$^{1\%}$) 235 (299), 255 (280), 297 (274).

NMR: $\delta^{DMSO-d6+D2O}$ ppm 1.46 (6H, s, C—CH$_3$), 3.38 (2H, s-br, 2-H), 4.90 and 5.40 (each 1H, d, J=19, 3-CH$_2$), 5.15 (1H, d, J=4.5, 6-H), 5.84 (1H, d, J=4.5, 7-H), 6.72 (1H, s, thiazole-H), 7.06 and 7.53 (each 1H, d, J=5, thiazole-H), 8.70 (1H, s, CHO).

EXAMPLE 15

7-[(Z)-2-(2-Aminothiazol-4-yl)-2-(2-carboxyprop-2-oxyimino)acetamido]-3-(2-methylaminothiazolio)methyl-3-cephem-4-carboxylate [Ip]

A mixture of diphenylmethyl 7-[(Z)-2-(2-t-butoxycarbonylprop-2-oxyimino)-2-(2-tritylaminothiazol-4-yl)acetamido]-3-iodomethyl-4-carboxylate (VII-4') (530 mg, 0.5 mmole) and 2-methylaminothiazole (114 mg, 1 mmole) [prepared according to the procedure described by E. Näf, Ann., 265, 108 (1892)] in DMSO (1 mL) was stirred for 3 days at 7° C. The mixture was diluted with water (10 mL) and extracted with ethyl acetate (30 mL). The extract was washed with water (3×10 mL), dried over MgSO$_4$ and evaporated to dryness under reduced pressure to give 400 mg of an oily residue. A mixture of the oil, TFA (4 mL) and anisole (1 drop) was stirred for 1 hour at room temperature and filtered. The filtrate was diluted with ether (30 mL) to give a precipitate which was collected by filtration. An aqueous solution of the solid was adjusted to pH 6 with NaHCO$_3$ and chromatographed on a PrepPAK 500/C$_{18}$ (100 mL)

column using water as eluant. Fractions containing the desired product were collected and evaporated in vacuo to afford 33 mg (11%) of the title product [Ip]. Mp. 200° C. (dec.).

IR: $\nu_{max}^{KBr}$ cm$^{-1}$ 3400, 1760, 1660, 1590.

UV: $\lambda_{max}^{Phosphate\ buffer\ (pH\ 7)}$ nm(E$_{1\ cm}^{1\%}$) 248 (314), 260 (300), 295 (127).

NMR: $\delta^{DMSO-d_6}$ ppm 1.4 (6H, s, C—CH$_3$), 2.91 (3H, s, N—CH$_3$), 5.00 (1H, d, J=4.5, 6-H), 5.65 (1H, d-d, J=4.5 and 7.5, 7-H), 6.64 (1H, s, thiazole-H), 7.46 (1H, d, J=4, thiazole-H).

EXAMPLE 16

7-[(Z)-2-(2-Aminothiazol-4-yl)-2-(2-carboxyprop-2-oxyimino)acetamido]-3-(4-methyl-2-methylthiothiazolio)methyl-3-cephem-4-carboxylate [Iq]

To a stirred solution containing benzhydryl 7-[(Z)-2-(2-t-butoxycarbonylprop-2-oxyimino)-2-(2-tritylamino-thiazol-4-yl)acetamido]-3-iodomethyl-4-carboxylate (VII-4′) (530 mg, 0.5 mmole) and 2-methylthio-4-methylthiazole (108 mg, 0.75 mmole) [prepared according to the procedure described by E. R. Buchanan et al., J. Org. Chem., 6, 764 (1941)] in dry CH$_2$Cl$_2$ (4 mL), was added silver tetrafluoroborate (90% pure, 108 mg, 0.5 mmole) at −20° C. The mixture was allowed to stir at room temperature for 1 hour and filtered through a glass microfiber paper (Whatman, GF/F). The filtrate was evaporated in vacuo to give an oily residue, which was triturated with ether (20 mL) to yield 530 mg of an amorphous powder. This material was purified by silica gel column chromatography, eluting with CHCl$_3$, CHCl$_3$—CH$_3$OH (100:1) and CHCl$_3$—CH$_3$OH (4:1), successively, to give the crude quaternized salt (220 mg). A mixture of the salt and anisole (0.1 mL) in TFA (1 mL) was stirred at ambient temperature for 1 hour and filtered through a glass microfiber paper, and the filter cake was washed with TFA. The filtrate and the wash were combined and evaporated under reduced pressure to give an oily residue, which was triturated with ether (30 mL) to yield 133 mg of the TFA salt. The salt (130 mg) was dissolved in water (4 mL) in the presence of NaHCO$_3$ and purified by column chromatography (μ-Bondpak), eluting with water, to give 40 mg (13%) of the title compound [Iq]. Estimated purity 70% (by HPLC). Mp. 148°–150° C. (dec.).

IR: $\nu_{max}^{KBr}$ cm$^{-1}$ 1765, 1600, 1535, 1400.

UV: $\lambda_{max}^{Phosphate\ buffer\ (pH\ 7)}$ nm($\epsilon$) 235 (16200), 258(sh) (15400), 300(sh) (14400).

NMR: $\delta^{D_2O}$ ppm 1.58 (6H, s, C—CH$_3$), 2.60 (3H, s, thiazole-4-CH$_3$), 3.05 (3H, s, thiazole-2-SCH$_3$), 3.35 (2H, s-like, 2-H), 5.90 (1H, m, 7-H), 7.04 (1H, s, thiazole-H), 7.64 (1H, s, thiazole-H).

EXAMPLE 17

7-[(Z)-2-(2-Aminothiazol-4-yl)-2-propargyloxyiminoacetamido]-3-(2-methylthiothiazolio)methyl-3-cephem-4-carboxylate [Ir]

To an ice-cooled solution of diphenylmethyl 7-[(Z)-2-propargyloxyimino-2-(2-tritylaminothiazol-4-yl)acetamido]-3-iodomethyl-3-cephem-4-carboxylate (VII-7) (519 mg, 0.54 mmole) and 2-methylthiothiazole (175 mg, 1.2 mmoles) in CH$_2$Cl$_2$ (10 mL) was added AgBF$_4$ (117 mg, 0.6 mmole), and the mixture was stirred for 1 hour. The reaction mixture was filtered and the filter cake was washed with CHCl$_3$ (50 mL). The filtrate and the washings were combined, washed with water, dried over MgSO$_4$ and evaporated. The residue was triturated with ether to give an amorphous solid (609 mg), which was dissolved in 90% TFA (5 mL). The solution was stirred for 1 hour at 0°–5° C. and evaporated in vacuo at 10° C. The residue was triturated with ether to give 350 mg of the crude product, which was dissolved in a small amount of methanol and chromatographed on a column of HP-20 (20 mL) (eluting with 30% aqueous methanol) to give 39 mg (13%) of the solid product. This was further purified by HPLC (Column: Lichrosorb RP-18, 8×300 mm) (eluting with 25% aqueous CH$_3$OH) to give 12 mg (4%) of the title compound [Ir]. Estimated purity 60% (by HPLC). Mp. 160° C. (dec.).

IR: $\nu_{max}^{KBr}$ cm$^{-1}$ 1765, 1610, 1535.

UV: $\lambda_{max}^{Phosphate\ buffer\ (pH\ 7)}$ nm($\epsilon$) 234 (17600), 258 (16400), 277 (15700).

NMR: $\delta^{D_2O}$ ppm 2.80 (1H, s, CH), 3.08 (3H, s, S—CH$_3$), 3.33 and 3.62 (each 1H, d, J=18, 2-H), 5.34 (1H, d, 6-H), 5.93 (1H, d, 7-H), 7.12 (1H, s, thiazole-H), 7.95 and 8.17 (each 1H, d, J=4, thiazole-H).

We claim:

1. A compound of the formula

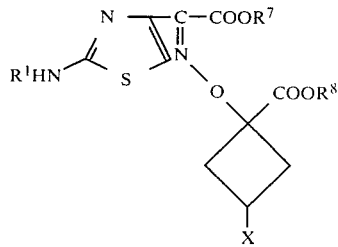

wherein R$^1$ is hydrogen or the trityl group, R$^7$ is hydrogen or (lower)alkyl, R$^8$ is hydrogen or the benzhydryl or t-butyl group and X is halogen, or, if R$^7$ or R$^8$ is hydrogen, a salt thereof.

2. (Z)-2-(1-t-Butoxycarbonyl-3-chlorocyclobut-1-oxyimino)-2-(2-tritylaminothiazol-4-yl)acetic acid, or a salt or (lower)alkyl ester thereof.

3. Ethyl (Z)-2-(1-t-butoxycarbonyl-3-chlorocyclobut-1-oxyimino)-2-(2-tritylaminothiazol-4-yl)acetate.

* * * * *